United States Patent
Koutnikova et al.

(10) Patent No.: US 8,273,548 B2
(45) Date of Patent: Sep. 25, 2012

(54) NUCLEIC ACIDS ENCODING A HUMAN PAP1 POLYPEPTIDE

(75) Inventors: Han Koutnikova, Ostwald (FR); Alexis Brice, Paris (FR); Alain Fournier, Chatenay Malabry (FR); Laurent Pradier, Verrieres (FR); Catherine Prades, Thiais (FR); Isabelle Arnould-Reguigne, Chennevieres sur Marne (FR); Marie-Françoise Rosier-Montus, Antony (FR); Olga Corti, Paris (FR)

(73) Assignee: Aventis Pharma S.A., Antony (FR)

( * ) Notice: Subject to any disclaimer, the term of this patent is extended or adjusted under 35 U.S.C. 154(b) by 868 days.

(21) Appl. No.: 11/390,195

(22) Filed: Mar. 28, 2006

(65) Prior Publication Data

US 2006/0287230 A1 Dec. 21, 2006

Related U.S. Application Data

(62) Division of application No. 09/785,548, filed on Feb. 20, 2001, now Pat. No. 7,132,396.

(60) Provisional application No. 60/198,489, filed on Apr. 18, 2000.

(30) Foreign Application Priority Data

Feb. 17, 2000 (FR) ...................................... 00 01980

(51) Int. Cl.
  *C12N 15/12* (2006.01)
  *C12N 15/63* (2006.01)
  *C12N 15/85* (2006.01)
  *C12N 1/21* (2006.01)

(52) U.S. Cl. .................. 435/69.1; 536/23.5; 435/320.1; 435/325; 435/252.3

(58) Field of Classification Search ........................ None
See application file for complete search history.

(56) References Cited

U.S. PATENT DOCUMENTS

2003/0220240 A1* 11/2003 Tang et al. ...................... 514/12

FOREIGN PATENT DOCUMENTS

WO WO 01/46256 A2 6/2001

OTHER PUBLICATIONS

Kitada, T., et al, Mutations in the parkin gene cause autosomal recessive juvenile parkinsonism, vol. 329, Apr. 9, 1998, pp. 605-608.
Abbas, N., et al, A wide variety of mutations in the parkin gene are responsible for autosomal recessive parkinsonism in Europe, Hum. Mol. Ganet., vol. 8, 1999, pp. 567-574.
Hattori, N., et al, Molecular genetic analysis of a novel Parkin gene in Japanese families with autosomal recessive juvenile parkinsonism, Ann. Neurol., vol. 6, 1998, pp. 935-941.
Lucking, C., et al, Homozygous deletions in parkin gene in European and North African families with autosomal recessive juvenile parkinsonism, Lancet, vol. 352, 1998, pp. 1355-1356.
Morett, E., et al, A novel transactivation domain in parkin, Trends Biochem Sci., vol. 24, 1999, pp. 229-231.
Polymeropoulos, M.H., et al, Mutation in the alpha-synuclein gene identified in families with Parkinson's disease, Science, vol. 276, 1997, pp. 2045-2047.
Shimura, H., et al, Immunohistochemical and subcellular localization of Parkin protein: absence of protein in autosomal recessive juvenile parkinsonism patients, Ann. Neurol., vol. 45, 1999, pp. 668-672.
Sunada, Y., et al, Differential expression of the parkin gene in the human brain and peripheral leukocytes, Neurosci Lett., vol. 254, 1998, pp. 180-182.
Mellick, G.D., et al, The parkin gene S/N167 polymorphism in Australian Parkinson's disease patients and controls, Parkinson and Related Disorders 7, 2001, pp. 89-91.
Rudinger, J., Peptide Hormones, (editor J. A. Parsons). University Park Press, Baltimore, 1976, pp. 1-7.
Stratagene Product Catalog, Product #300071, La Jolla, CA, pp. 95, 1991.

* cited by examiner

Primary Examiner — Robert C Hayes
(74) Attorney, Agent, or Firm — Wiley Rein LLP

(57) ABSTRACT

The present invention relates to novel compounds and their uses, in particular their pharmaceutical or diagnostic uses or their use as pharmacological targets. More particularly, the present invention relates to a novel protein, referred to as PAP1, as well as to novel peptides and compounds which are capable of modulating, at least partially, the activity of parkin.

7 Claims, 11 Drawing Sheets

Figure 1:
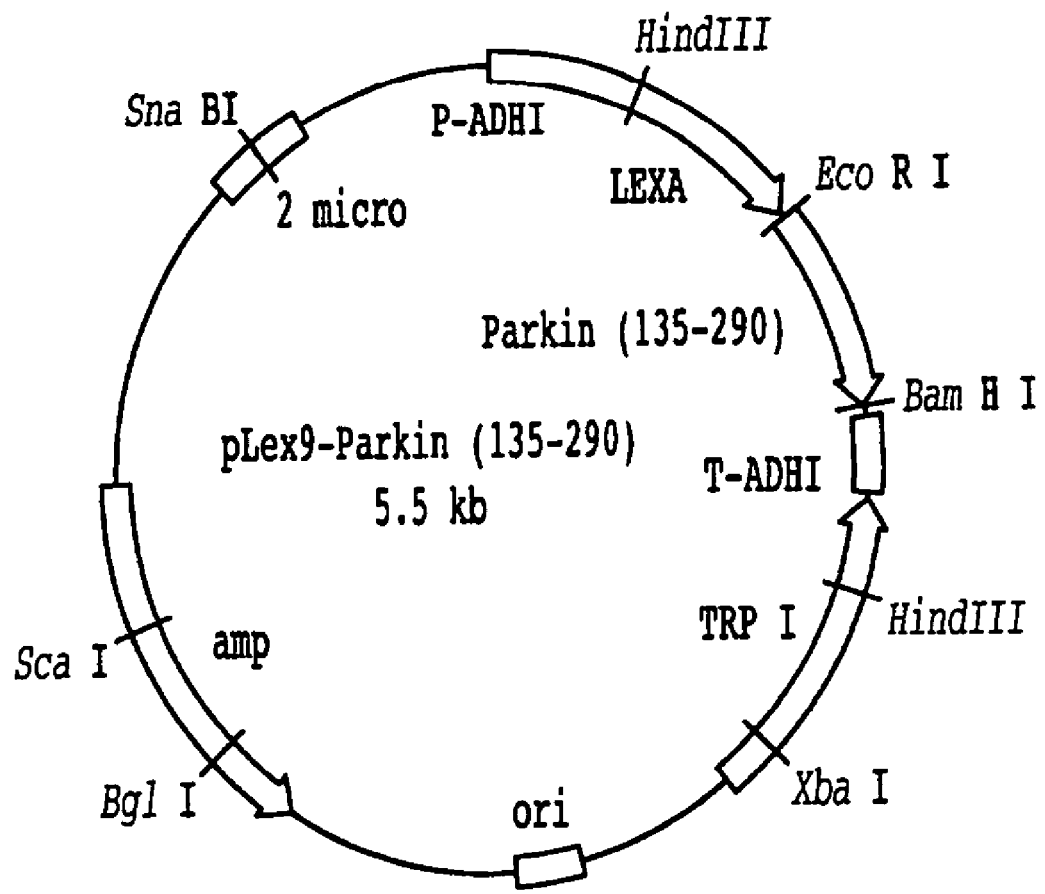

Ly111b-fullA : the transcript (SEQ ID NO: 47)

AATGGAAGGGCGTGAGCGCTTGGTCCATGCAGTGAAGCTCTTCCAACCTGGGTCAACGAAAACGGAGAAGAAATGGCCCA
AGAAATAGATCTGAGTGCTCTCAAGGAGTTAGAACGCGAGGCCATTCTCCAGGTCCTGTACCGAGACCAGGCGGTTCAAA
ACACAGAGGAGGAGAGGACACGGAAACTGAAAACACACCTGCAGCATCTCCGGTGGAAAGGAGCGAAGAACACGGACTGG
GAGCCACAAAGAGAAGTGCTGTGCGCGCTGCCAGCAGGTGCTGGGGTTCCTGCTGCACCGGGGCGCCGTGTGCCGGGGCTG
CAGCCACCGCGTGTGTGCCCAGTGCCGAGTGTTCCTGAGGGGGACCCATGCCTGGAAGTGCACGGTGTGCTTCGAGGACA
GGAATGTCAAAATAAAAACTGGAGAATGGTTCTATGAGGAACGAGCCAAGAAATTTCCAACTGGAGGCAAACATGAGACA
GTTGGAGGGCAGCTCTTGCAATCTTATCAGAAGCTGAGCAAAATTTCTGTGGTTCCTCCTACTCCACCTCCTGTCAGCGA
GAGCCAGTGCAGCCGCAGTCCTGGCAGGTTACAGGAATTTGGTCAGTTTAGAGGATTTAATAAGTCCGTGGAAAATTTGT
TTCTGTCTCTTGCTACCCACGTGAAAAAGCTCTCCAAATCCCAGAATGATATGACTTCTGAGAAGCATCTTCTCGCCACG
GGCCCCAGGCAGTGTGTGGGACAGACAGAGAGACGGAGCCAGTCTGACACTGCGGTCAACGTCACCACCAGGAAGGTCAG
TGCACCAGATATTCTGAAACCTCTCAATCAAGAGGATCCCAAATGCTCTACTAACCCTATTTTGAAGCAACAGAATCTCC
CATCCAGTCCGGCACCCAGTACCATATTCTCTGGAGGTTTTAGACACGGAAGTTTAATTAGCATTGACAGCACCTGTACA
GAGATGGGCAATTTTGACAATGCTAATGTCACTGGAGAAATAGAATTTGCCATTCATTATTGCTTCAAAACCCATTCTTT
AGAAATATGCATCAAGGCCTGTAAGAACCTTGCCTATGGAGAAGAAAAGAAGAAAAAGTGCAATCCGTATGTGAAGACCT
ACCTGTTGCCCGACAGATCCTCCCAGGGAAAGCGCAAGACTGGAGTCCAAAGGAACACCGTGGACCCGACCTTTCAGGAG
ACCTTGAAGTATCAGGTGGCCCCTGCCCAGCTGGTGACCCGGCAGCTGCAGGTCTCCGGTGTGGCATCTGGGCACGCTGGC
CCGGAGAGTGTTTCTTGGAGAAGTGATCATTCCTCTGGCCCACGTGGGACTTTGAAGACAGCACAACACAGTCCTTCCGCT
GGCATCCGCTCCGGGCCAAGGCGGAGAAATACGAAGACAGCGTTCCTCAGAGTAATGGAGAGCTCACAGTCCGGGCTAAG
CTGGTTCTCCCTTCACGGCCCAGAAAACTCCAAGAGGCTCAAGAAGGGACAGATCAGCCATCACTTCATGGTCAACTTTG
TTTGGTAGTGCTAGGAGCCAAGAATTTACCTGTGCGGCCAGATGGCACCTTGAACTCATTTGTTAAGGGCTGTCTCACTC
TGCCAGACCAACAAAAACTGAGACTGAAGTCGCCAGTCCTGAGGAAGCAGGCTTGCCCCCAGTGGAAACACTCATTTGTC
TTCAGTGGCGTAACCCCAGCTCAGCTGAGGCAGTCGAGCTTGGAGTTAACTGTCTGGGATCAGGCCCTCTTTGGAATGAA
CGACCGCTTGCTTGGAGGAACCAGACTTGGTTCAAAGGGAGACACAGCTGTTGGCGGGGATGCATGCTCACAATCGAAGC
TCCAGTGGCAGAAAGTCCTTTCCAGCCCCAATCTATGGACAGACATGACTCTTGTCCTGCACTGACATGAAGGCCTCAAG
GTTCCAGGTTGCAGCAGGCGTGAGG pLy111b-fullA : the protein (SEQ ID NO: 48)

MAQEIDLSALKELEREAILQVLYRDQAVQNTEEERTRKLKTHLQHLRWKGAKNTDWEHKEKCCARCQQVLGFLLHRGAVC
RGCSHRVCAQCRVFLRGTHAWKCTVCFEDRNVKIKTGEWFYEERAKKFPTGGKHETVGGQLLQSYQKLSKISVVPPTPPP
VSESQCSRSPGRLQEFGQFRGFNKSVENLFLSLATHVKKLSKSQNDMTSEKHLLATGPRQCVGQTERRSQSDTAVNVTTR
KVSAPDILKPLNQEDPKCSTNPILKQQNLPSSPAPSTIFSGGFRHGSLISIDSTCTEMGNFDNANVTGEIEFAIHYCFKT
HSLEICIKACKNLAYGEEKKKKCNPYVKTYLLPDRSSQGKRKTGVQRNTVDPTFQETLKYQVAPAQLVTRQLQVSVWHLG
TLARRVFLGEVIIPLATWDFEDSTTQSFRWHPLRAKAEKYEDSVPQSNGELTVRAKLVLPSRPRKLQEAQEGTDQPSLHG
QLCLVVLGAKNLPVRPDGTLNSFVKGCLTLPDQQKLRLKSPVLRKQACPQWKHSFVFSGVTPAQLRQSSLELTVWDQALF
GMNDRLLGGTRLGSKGDTAVGGDACSQSKLQWQKVLSSPNLWTDMTLVLH

FIG. 6

Ly111b-fullB : the transcript (SEQ ID NO: 49)

```
AATGGAAGGGCGTGAGCGCTTGGTCCATGCAGTGAAGCTCTTCCAACCTGGGTCAACGAAAACGGAGAAGAAATGGCCCA
AGAAATAGATCTGAGTGCTCTCAAGGAGTTAGAACGCGAGGCCATTCTCCAGGTCCTGTACCGAGACCAGGCGGTTCAAA
ACACAGAGGAGGAGAGGACACGGAAACTGAAAACACACCTGCAGCATCTCCGGTGGAAAGGAGCGAAGAACACGGACTGG
GAGCACAAAGAGAAGTGCTGTGCGCGCTGCCAGCAGGTGCTGGGGTTCCTGCTGCACCGGGGCGCCGTGTGCCGGGGCTG
CAGCCACCGCGTGTGTGCCCAGTGCCGAGTGTTCCTGAGGGGGACCCATGCCTGGAAGTGCACGGTGTGCTTCGAGGACA
GGAATGTCAAAATAAAAACTGGAGAATGGTTCTATGAGGAACGAGCCAAGAAATTTCCAACTGGAGGCAAACATGAGACA
GTTGGAGGGCAGCTCTTGCAATCTTATCAGAAGCTGAGCAAAATTTCTGTGGTTCCTCCTACTCCACCTCCTGTCAGCGA
GAGCCAGTGCAGCCGCAGTCCTGGCAGGAAGGTCAGTGCACCAGATATTCTGAAACCTCTCAATCAAGAGGATCCCAAAT
GCTCTACTAACCCTATTTTGAAGCAACAGAATCTCCCATCCAGTCCGGCACCCAGTACCATATTCTCTGGAGGTTTTAGA
CACGGAAGTTTAATTAGCATTGACAGCACCTGTACAGAGATGGGCAATTTTGACAATGCTAATGTCACTGGAGAAATAGA
ATTTGCCATTCATTATTGCTTCAAAACCCATTCTTTAGAAATATGCATCAAGGCCTGTAAGAACCTTGCCTATGGAGAAG
AAAAGAAGAAAAAGTGCAATCCGTATGTGAAGACCTACCTGTTGCCCGACAGATCCTCCCAGGGAAAGCGCAAGACTGGA
GTCCAAAGGAACACCGTGGACCCGACCTTTCAGGAGACCTTGAAGTATCAGGTGGCCCCTGCCCAGCTGGTGACCCGGCA
GCTGCAGGTCTCGGTGTGGCATCTGGGCACGCTGGCCCGGAGAGTGTTTCTTGGAGAAGTGATCATTCCTCTGGCCACGT
GGGACTTTGAAGACAGCACAACACAGTCCTTCCGCTGGCATCCGCTCCGGGCCAAGGCGGAGAAATACGAAGACAGCGTT
CCTCAGAGTAATGGAGAGCTCACAGTCCGGGCTAAGCTGGTTCTCCCTTCACGGCCCAGAAAACTCCAAGAGGCTCAAGA
AGGGACAGATCAGCCATCACTTCATGGTCAACTTTGTTTGGTAGTGCTAGGAGCCAAGAATTTACCTGTGCGGCCAGATG
GCACCTTGAACTCATTTGTTAAGGGCTGTCTCACTCTGCCAGACCAACAAAAACTGAGACTGAAGTCGCCAGTCCTGAGG
AAGCAGGCTTGCCCCCAGTGGAAACACTCATTTGTCTTCAGTGGCGTAACCCCAGCTCAGCTGAGGCAGTCGAGCTTGGA
GTTAACTGTCTGGGATCAGGCCCTCTTTGGAATGAACGACCGCTTGCTTGGAGGAACCAGACTTGGTTCAAAGGGAGACA
CAGCTGTTGGCGGGGATGCATGCTCACAATCGAAGCTCCAGTGGCAGAAAGTCCTTTCCAGCCCAATCTATGGACAGAC
ATGACTCTTGTCCTGCACTGACATGAAGGCCTCAAGGTTCCAGGTTGCAGCAGGCGTGAGG
``` pLy111b-fullB : the protein (SEQ ID NO: 50)

```
MAQEIDLSALKELEREAILQVLYRDQAVQNTEEERTRKLKTHLQHLRWKGAKNTDWEHKEKCCARCQQVLGFLLHRGAVC
RGCSHRVCAQCRVFLRGTHAWKCTVCFEDRNVKIKTGEWFYEERAKKFPTGGKHETVGGQLLQSYQKLSKISVVPPTPPP
VSESQCSRSPGRKVSAPDILKPLNQEDPKCSTNPILKQQNLPSSPAPSTIFSGGFRHGSLISIDSTCTEMGNFDNANVTG
EIEFAIHYCFKTHSLEICIKACKNLAYGEEKKKKCNPYVKTYLLPDRSSQGKRKTGVQRNTVDPTFQETLKYQVAPAQLV
TRQLQVSVWHLGTLARRVFLGEVIIPLATWDFEDSTTQSFRWHPLRAKAEKYEDSVPQSNGELTVRAKLVLPSRPRKLQE
AQEGTDQPSLHGQLCLVVLGAKNLPVRPDGTLNSFVKGCLTLPDQQKLRLKSPVLRKQACPQWKHSFVFSGVTPAQLRQS
SLELTVWDQALFGMNDRLLGGTRLGSKGDTAVGGDACSQSKLQWQKVLSSPNLWTDMTLVLH
```

FIG. 7

Ly111b-fullB : the transcript

```
GGCCTTGGGGCACTGAGGGATGCCAGTTCTGCCTGTTCATCTGGAACCTGGATCTAAGGAGGGAAGAG
GCGTTGCCCCTGCTGGCATAGTCAGGTACCAGCCCAGCCAGGTATTGAACGGGCTGAGCTTTTCATGA
TGGTTCCTGCTGACCTGGAAACATCTTAAATGGAAGGGCGTGAGCGCTTGGTCCATGCAGTGAAGCTC
TTCCAACCTGGGTCAACGAAAACGGAGAAGAAATGGCCCAAGAAATAGATCTGAGTGCTCTCAAGGAG
TTAGAACGCGAGGCCATTCTCCAGGTCCTGTACCGAGACCAGGCGGTTCAAAACACAGAGGAGGAGAG
GACACGGAAACTGAAAACACACCTGCAGCATCTCCGGTGGAAAGGAGCGAAGAACACGGACTGGGAGC
ACAAAGCGAAGTGCTGTGCGCGCTGCCAGCAGGTGCTGGGGTTCCTGCTGCACCGGGGCGCCGTGTGC
CGGCGCTGCAGCCACCGCGTGTGTGCCCAGTGCCGAGTGTTCCTGAGGGGGACCCATGCCTGGAAGTG
CACGGTGTGCTTCGAGGACAGCAATGTCAAAATAAAAACTGGAGAATGGTTCTATGAGGAACGAGCCA
AGAAATTTCCAACTGGAGGCAAACATGAGACAGTTGGAGGGCAGCTCTTGCAATCTTATCAGAAGCTG
AGCAAAATTTCTGTGGTTCCTCCTACTCCACCTCCTGTCAGCGAGAGCCAGTGCAGCCGCAGTCCTGG
CAGGTTACAGGAATTTCCTCACTTTAGAGGATTTAATAAGTCCGTGGAAAATTTGTTTCTGTCTCTTG
CTACCCACGTGAAAAAGCTCTCCAAATCCCAGAATGATATGACTTCTGAGAAGCATCTTCTCGCCACG
GGCCCCAGGCAGTGTGTGGGACAGACAGAGAGACGGAGCCAGTGTGACACTGCGGTCAACGTCACCAC
CAGGAAGGTCAGTGCACCAGATATTCTGAAACCTCTCAATCAAGAGGATCCCAAATGCTCTACTAACC
CTATTTTGAAGCAACAGAATCTCCCATCCAGTCCGGCACCCAGTACCATATTCTCTGGAGGTTTTAGA
CACGGAAGTTTAATTAGCATTGACAGCACCTGTACAGAGATGGGCAATTTTGACAATGCTAATGTCAC
TGGAGAAATAGAATTTGCCATTCATTATTGCTTCAAAACCCATTCTTTAGAAATATGCATCAAGGCCT
GTAAGAACCTTGCCTATGGAGAAGAAAAGAAGAAAAAGTGCAATCCGTATGTGAAGACCTACCTGTTG
CCCGACAGATCCTCCCAGGGAAAGCGCAAGACTGGAGTCCAAAGGAACACCGTGGACCCGACCTTTCA
GGAGACCTTGAAGTATCAGGTGGCCCCTGCCCAGCTGGTGACCCGGCAGCTGCAGGTCTCGGTGTGGC
ATCTGGGCACGCTGGCCCGGAGAGTGTTTCTTGGAGAAGTGATCATTCCTCTGGCCACGTGGGACTTT
GAAGACAGCACAACACAGTCCTTCCGCTGGCATCCGCTCCGGGCCAAGGCGGAGAAATACGAAGACAG
CGTTCCTCAGAGTAATGGAGAGCTCACAGTCCGGGCTAAGATGGTTCTCCCTTCACGGCCCAGAAAAC
TCCAAGAGGCTCAAGAAGGGACAGATCAGCCATCACTTCATGGTCAACTTTCTTTGGTAGTGCTAGGA
GCCAAGAATTTACCTGTGCGGCCAGATGGCACCTTGAACTCATTTGTTAAGGCCTGTCTCACTCTGCC
AGACCAACAAAAACTGAGACTGAAGTCGCCAGTCCTGAGGAAGCAGGCTTGCCCCCAGTGGAAACACT
CATTTGTCTTCAGTGGCGTAACCCCAGCTCAGCTGAGGCAGTCGAGCTTGGAGTTAACTGTCTGGGAT
CAGGCCCTCTTTGGAATGAACGACCGCTTGCTTGGAGGAACCAGACTTGGTTCAAAGGGAGACACAGC
TGTTGGCGGGGATGCATGCTCACAATCGAAGCTCCAGTGGCAGAAAGTCCTTTCCAGCCCCAATCTAT
GGACAGACATGACTCTTGTCCTGCACTGACATGAAGGCCTCAAGGTTCCAGCTTGCAGCAGGCGTGAG
GCACTGTGCGTCTGCAGAGGGGCTACGAACCAGGTGCAGGGTCCCAGCTGGAGACCCCTTTGACCTTG
AGCAGTCTCCATCTGCGGCCCTGTCCCATGGCTTAACCGCCTATTGGTATCTGTGTATATTTACGTTA
AACACAATTATGTTACCTAAGCCTCTGGTGGGTTATCTCCTCTTTGAGATGTAGAAAATGGCCAGATT
TTAATAAACGTTGTTACCCATGAAAAAAAAAAAAA
```

: the protein

```
MAQEIDLSALKELEREAILQVLYRDQAVQNTEEERTRKLKTHLQHLRWKGAKNTDWEHKEKCCARCQQ
VLGFLLHRGAVCRGCSHRVCAQCRVFLRGTHAWKCTVCFEDRNVKIKTGEWFYEERAKKFPTGGKHET
VGGQLLQSYQKLSKISVVPPTPPPVSESQCSRSPGRLQEFGQFRGFNKSVENLFLSLATHVKKLSKSQ
NDMTSEKHLLATGPRQCVGQTERRSQSDTAVNVTTRKVSAPDILKPLNQEDPKCSTNPILKQQNLPSS
PAPSTIFSGGFRHGSLISIDSTCTEMGNFDNANVTGEIEFAIHYCFKTHSLEICIKACKNLAYGEEKK
KKCNPYVKTYLLPDRSSQGKRKTGVQRNTVDPTFQETLKYQVAPAQLVTRQLQVSVWHLGTLARRVFL
GEVIIPLATWDFEDSTTQSFRWHPLRAKAEKYEDSVPQSNGELTVRAKLVLPSRPRKLQEAQEGTDQP
SLHGQLCLVVLGAKNLPVRPDGTLNSFVKGCLTLPDQQKLRLKSPVLRKQACPQWKHSFVFSGVTPAQ
LRQGSLELTVWDQALFGMNDRLLGGTRLGSKGDTAVGGDACSQSKLQWQKVLSSPNLWTDMTLVLH
```

FIG. 9

: the transcript

GAAATCATGCCCCTCGTAGAGCAGCAGGTCCAAGCAGGGCTGCTGGCTATTTTTCCAAAAAG
TGAGGCAGTTTAAAAAAAAGGCGGAGAACTAGAATTATAGAATAATGGCACATTTTGTGTAT
TTGTAAAACTAACGCCTTGCATGGTTCACAACCCATTTCTTATGCCTGTGTTTTCCTTGGCA
GCAAAATTTCTGTGGTTCCTCCTACTCCACCTCCTGTCAGCGAGAGCCAGTGCAGCCGCAGT
CCTGGCAGGAAGGTCAGTGCACCAGATATTCTGAAACCTCTCAATCAAGAGGATCCCAAATG
CTCTACTAACCCTATTTTGAAGCAACAGAATCTCCCATCCAGTCCGGCACCCAGTACCATAT
TCTCTGGAGGTTTTAGACACCCAACTTTAATTACCATTGACAGCACGTGTACAGAGATGGGC
AATTTTGACAATGCTAATGTCACTGGAGAAATAGAATTTGCCATTCATTATTGCTTCAAAAC
CCATTCTTTAGAAATATGCATCAAGGCCTGTAAGAACCTTGCCTATGGAGAAGAAAAGAAGA
AAAGTGCAATCCGTATGTGAAGACCTACCTGTTGCCCGACAGATCCTCCCAGGGAAAGCGC
AAGACTGGAGTCCAAAGGAACACCGTGGACCCGACCTTTCAGGAGACCTTGAAGTATCAGGT
GGCCCCTGCCCAGCTGGTGACCCGGCAGCTGCAGGTCTCGGTGTGGCATCTGGGCACGCTGG
CCCGGAGAGTGTTTCTTGGAGAAGTGATCATTCCTCTGGCCACGTGGGACTTTGAAGACAGC
ACAACACAGTCCTTCCGCTGGCATCCGCTCCGGGCCAAGGCGGAGAAATACGAAGACAGCGT
TCCTCAGAGTAATGGAGAGCTCACAGTCCGGGCTAAGCTGGTTCTCCCTTCACGGCCCAGAA
AACTCCAAGAGGCTCAAGAAGGGACAGATCAGCCATCACTTCATGGTCAACTTTGTTTGGTA
GTGCTAGGAGCCAAGAATTTACCTGTGCGGCCAGATGGCACCTTGAACTCATTTGTTAAGGG
CTGTCTCACTCTGCCAGACCAACAAAAACTGAGACTGAAGTCGCCAGTCCTGAGGAAGCAGG
CTTGCCCCCAGTGGAAACACTCATTTGTCTTCAGTGGCGTAACCCCAGCTCAGCTGAGGCAG
TCGAGCTTGGAGTTAACTGTCTGGGATCAGGCCCTCTTTGGAATGAACGACCGCTTGCTTGG
AGGAACCAGACTTGGTTCAAAGGGAGACACAGCTGTTGGCGGGGATGCATGCTCACAATCGA
AGCTCCAGTGGCAGAAAGTCCTTTCCAGCCCCAATCTATGGACAGACATGACTCTTGTCCTG
CACTGACATGAAGGCCTCAAGGTTCCAGGTTGCAGCAGGCGTGAGGCACTGTGCGTCTGCAG
AGGGGCTACGAACCAGGTGCAGGGTCCCAGCTGGAGACCCCTTTGACCTTGAGCAGTCTCCA
TCTGCGGCCCTGTCCCATGGCTTAACCGCCTATTGGTATCTGTGTATATTTACGTTAAACAC
AATTATGTTACCTAAGCCTCTGGTGGGTTATCTCCTCTTTGAGATGTAGAAAATGGCCAGAT
TTTAATAAACGTTGTTACCCATGAAAAAAAAAAAAA

: the protein

MGNFDNANVTGEIEFAIHYCFKTHSLEICIKACKNLAYGEEKKKKCNPYVKTYLLPDRSSQG
KRKTGVQRNTVDPTFQETLKYQVAPAQLVTRQLQVSVWHLGTLARRVFLGEVIIPLATWDFE
DSTTQSFRWHPLRAKAEKYEDSVPQSNGELTVRAKLVLPSRPRKLQEAQEGTDQPSLHGQLC
LVVLGAKNLPVRPDGTLNSFVKGCLTLPDQQKLRLKSPVLRKQACPQWKHSFVFSGVTPAQL
RQSSLELTVWDQALFGMNDRLLGGTRLGSKGDTAVGGDACSQSKLQWQKVLSSPNLWTDMTL
VLH

FIG. 10

NUCLEIC ACIDS ENCODING A HUMAN PAP1 POLYPEPTIDE

This application is a divisional of U.S. application Ser. No. 09/785,548, filed Feb. 20, 2001 now U.S. Pat. No. 7,132,396, which claims priority to U.S. Provisional Application No. 60/198,489, filed Apr. 18, 2000, and French Application FR 00 01980, filed Feb. 17, 2000.

The present invention relates to compositions and methods which can be used for regulating the activity of parkin. It relates in particular to a novel protein, referred to as PAP1, which is a partner of parkin, as well as to the peptides or polypeptides which are derived from or are homologous to this protein. It also relates to compounds which are capable of modulating, at least partially, the activity of parkin, in particular of interfering with the interaction between parkin and PAP1. The present invention can be used in the therapeutic or diagnostic areas, or for forming pharmacological targets which make possible the development of novel drugs.

The parkin gene is mutated in certain familial forms (autosomal recessive juvenile) of Parkinson's disease (Kitada et al., 1998). Parkinson's disease (Lewy, 1912) is one of the most common neurodegenerative diseases, affecting more than 1% of the population over 55 years old. Patients suffering from this disease have neurological disorders which are grouped together under the term "Parkinsonian syndrome," which is characterized by rigidity, bradykinesia, and resting tremor. These symptoms are the consequence of a degeneration of the dopaminergic neurons of the substantia nigra of the brain.

Most cases with a Parkinson's disease do not have a familial history. However, familial cases do exist, of which certain correspond to a monogenic form of the disease. At the current time, only three different genes have been identified in certain rare hereditary forms. The first form corresponds to an autosomal dominant form, in which the gene responsible encodes alpha Synuclein (Polymeropoulos et al., 1997). This protein is an abundant constituent of the intracytoplasmic inclusions, termed Lewy bodies, which are used as a marker for Parkinson's disease (Lewy, 1912). The second form, also autosomal dominant, is linked to a mutation in a gene which encodes a hydrolase termed ubiquitin carboxy-terminal hydrolase L1 (Leroy et al., 1998). This enzyme is assumed to hydrolyze ubiquitin polymers or conjugates into ubiquitin monomers. The third form differs from the previous forms in that it has an autosomal recessive transmission and onset which often occurs before 40 years of age, as well as an absence of Lewy bodies. These patients respond more favorably to levodopa, a dopamine precursor which is used as treatment for Parkinson's disease. The gene involved in this form encodes a novel protein which is termed parkin (Kitada et al., 1998).

The parkin gene consists of 12 exons which cover a genomic region of more than 500,000 base pairs on chromosome 6 (6q25.2-q27). At the current time, two major types of mutation of this gene, which are at the origin of the disease, are known; either deletions of variable size in the region which covers exons 2 to 9, or point mutations which produce the premature appearance of a stop codon or the change of an amino acid (Kitada et al., 1998; Abbas et al., 1999; Lucking et al., 1998; Hattori et al., 1998). The nature of these mutations and the autosomal recessive method of transmission suggest a loss of function of the parkin, which leads to Parkinson's disease.

This gene is expressed in a large number of tissues and in particular in the substantia nigra. Several transcripts which correspond to this gene and originate from different alternative splicing sites Kitada et al., 1998; Sunada et al., 1998) exist. In the brain, two types of messenger RNAs are found, of which one lacks the portion corresponding to exon 5. In the leukocytes, parkin messenger RNAs which do not contain the region encoding exons 3, 4 and 5 have been identified. The longest of the parkin messenger RNAs, which is present in the brain, contains 2960 bases and encodes a protein of 465 amino acids.

This protein has a slight homology with ubiquitin in its N-terminal portion. Its C-terminal half contains two ring finger motifs, separated by an IBR (In Between Ring) domain, which correspond to a cysteine-rich region and which are able to bind metals, like the zinc finger domains (Morett, 1999). It has been shown by immunocytochemistry that parkin is located in the cytoplasm and the Golgi apparatus of neurons of the substantia nigra which contain melanin (Shimura et al., 1999). In addition, this protein is present in certain Lewy bodies of Parkinsonians.

The cellular function of parkin has not yet been demonstrated, but it might play a transporter role in synaptic vesicles, in the maturation or degradation of proteins, and in the control of cellular growth, differentiation or development. In the autosomal recessive juvenile forms, parkin is absent, which thus confirms that the loss of this function is responsible for the disease.

The elucidation of the exact role of the parkin protein in the process of degeneration of the dopaminergic neurons thus constitutes a major asset for the understanding of and the therapeutic approach to Parkinson's disease, and more generally diseases of the central nervous system.

The present invention lies in the identification of a partner of parkin, which interacts with this protein under physiological conditions. This partner represents a novel pharmacological target for manufacturing or investigating compounds which are capable of modulating the activity of parkin, in particular its activity on the degeneration of dopaminergic neurons and/or the development of nervous pathologies. This protein, the antibodies, the corresponding nucleic acids, as well as the specific probes or primers, can also be used for detecting or assaying the proteins in biological samples, in particular nervous tissue samples. These proteins or nucleic acids can also be used in therapeutic approaches, for modulating the activity of parkin and any compound according to the invention which is capable of modulating the interaction between parkin and the polypeptides of the invention.

The present invention results more particularly from the demonstration by the applicant of a novel human protein, referred to as PAP1 (Parkin Associated Protein 1), or LY111, which interacts with parkin. The PAP1 protein (sequence SEQ ID NO: 1 or 2) shows a certain homology with synaptotagmins and is capable of interacting more particularly with the central region of parkin (represented on the sequence SEQ ID NO: 3 or 4). The PAP1 protein has also been cloned, sequenced and characterized from various tissues of human origin, specifically lung and brain (SEQ ID NO: 12, 13) tissue, as well as short forms, which correspond to splicing variants (SEQ ID NO: 14, 15).

The present invention also results from the identification and characterization of specific regions of the PAP1 protein which are involved in the modulation of the function of parkin. The demonstration of the existence of this protein and of regions which are involved in its function makes it possible in particular to prepare novel compounds and/or compositions which can be used as pharmaceutical agents, and to develop industrial methods of screening such compounds.

A first subject of the invention thus relates to compounds which are capable of modulating, at least partially, the interaction between the PAP1 protein (or homologs thereof) and parkin (in particular human parkin), or of interfering with the interaction between these proteins.

Another subject of the invention lies in the PAP1 protein and fragments, derivatives and homologs thereof.

Another aspect of the invention lies in a nucleic acid which encodes the PAP1 protein or fragments, derivatives or homologs thereof, as well as any vector which comprises such a nucleic acid and any recombinant cell which contains such a nucleic acid or vector, and any non-human mammal comprising such a nucleic acid in its cells.

The invention also relates to antibodies which are capable of binding the PAP1 protein and fragments, derivatives and homologs thereof, in particular polyclonal or monoclonal antibodies, more preferably antibodies which are capable of binding the PAP1 protein and of inhibiting, at least partially, its interaction with parkin.

Another aspect of the invention relates to nucleotide probes or primers, which are specific to PAP1 and which can be used for detecting or amplifying the PAP1 gene, or a region of this gene, in any biological sample.

The invention also relates to pharmaceutical compositions, methods for detecting genetic abnormalities, methods for producing polypeptides as defined above and methods for screening or for characterizing active compounds.

As indicated above, a first aspect of the invention lies in a compound which is capable of interfering, at least partially, with the interaction between the PAP1 protein (or homologs thereof) and parkin.

For the purposes of the present invention, the name PAP1 protein refers to the protein per se, as well as to all homologous forms thereof. "Homologous form" is intended to refer to any protein which is equivalent to the protein under consideration, of varied cellular origin and in particular derived from cells of human origin, or from other organisms, and which possesses an activity of the same type. Such homologs also comprise natural variants of the PAP1 protein of sequence SEQ ID NO: 2, in particular polymorphic or splicing variants. Such homologs can be obtained by experiments of hybridization between the coding nucleic acids (in particular the nucleic acid of sequence SEQ ID NO: 1). For the purposes of the invention, a sequence of this type only has to have a significant percentage of identity to lead to a physiological behavior which is comparable to that of the PAP1 protein as claimed. "Significant percentage of identity" is intended to refer to a percentage of at least 60%, preferably 80%, more preferably 90% and even more preferably 95%. As such, variants and/or homologs of the sequence SEQ ID NO: 2 are described in the sequences SEQ ID NO: 13 and 15, and are identified from tissues of human origin. The name PAP1 therefore also encompasses these polypeptides.

For the purposes of the present invention, the "percentage of identity" between two sequences of nucleotides or amino acids can be determined by comparing two optimally aligned sequences through a window of comparison.

The part of the nucleotide or polypeptide sequence in the window of comparison can thus comprise additions or deletions (gaps, for example) as compared to the reference sequence (which does not contain these additions or deletions) such that an optimal alignment of the two sequences is obtained.

The percentage is calculated by determining the number of positions at which a nucleic acid base or identical amino acid residue is observed for the two sequences (nucleic acid or peptide) being compared, then dividing the number of positions at which there is identity between the two amino acid residues or bases by the total number of positions in the window of comparison, then multiplying the result by 100 so as to obtain the sequence identity percentage.

Optimal alignment of the sequences for purposes of the comparison can be performed on a computer using known algorithms contained in the Wisconsin Genetics Software Package, produced by Genetics Computer Group (GCG), 575 Science Dr., Madison, Wis.

For purposes of illustration, the sequence identity percentage may be obtained with the BLAST software (BLAST versions 1.4.9 of March 1996, 2.0.4 of February 1998 and 2.0.6 of September 1998) using only the default parameters (Altschul et al, *J. Mol. Biol.* (1990) 215:403-410; Altschul et al, *Nucleic Acids Res.* (1997) 25: 3389-3402). Blast searches for sequences which are similar/homologous to a reference "query" sequence, using the Altschul et al algorithm (above). The query sequence and the databases used can be peptide or nucleic acid, with any combination being possible.

The interference of a compound according to the invention can reveal itself in various ways. Thus, the compound can slow, inhibit or stimulate, at least partially, the interaction between the PAP1 protein, or a homologous form thereof, and parkin. Preferably, they are compounds which are capable of modulating this interaction in vitro, for example in a double-hybrid type system or in any a cellular system for detecting an interaction between two polypeptides. The compounds according to the invention are preferably compounds which are capable of modulating, at least partially, this interaction, preferably of increasing or inhibiting this reaction by at least 20%, more preferably by at least 50%, as compared to a control in the absence of the compound.

In a particular embodiment, they are compounds which are capable of interfering with the interaction between the region of parkin which is represented on the sequence SEQ ID NO: 4 and the region of the PAP1 protein which is represented on the sequence SEQ ID NO: 2, 13 and 15.

According to a particular embodiment of the invention, the compounds are capable of binding at the domain of interaction between the PAP1 protein, or a homologous form thereof, and parkin.

The compounds according to the present invention can be varied in nature and in origin. In particular, they can be compounds of peptide, nucleic acid (i.e. comprising a string of bases, in particular a DNA or an RNA molecule), lipid or saccharide type, an antibody, etc. and, more generally, any organic or inorganic molecule.

According to a first variation, the compounds of the invention are peptide in nature. The term "peptide" refers to any molecule comprising a string of amino acids, such as for example a peptide, a polypeptide, a protein or an antibody (or antibody fragment or derivative), which, if necessary, is modified or combined with other compounds or chemical groups. In this respect, the term "peptide" refers more specifically to a molecule comprising a string of at most 50 amino acids, more preferably of at most 40 amino acids. A polypeptide (or a protein) preferably comprises from 50 to 500 amino acids, or more.

According to a first preferred embodiment, the compounds of the invention are peptide compounds comprising all or part of the peptide sequence SEQ ID NO: 2 or a derivative thereof, in particular all or part of the peptide sequence SEQ ID NO: 13 and 15 or derivatives of these sequences, more particularly of the PAP1 protein, which comprises the sequence SEQ ID NO: 2, 13 and 15.

For the purposes of the present invention, the term "derivative" refers to any sequence which differs from the sequence under consideration because of a degeneracy of the genetic code, which is obtained by one or more modifications of genetic and/or chemical nature, as well as any peptide which is encoded by a sequence which hybridizes with the nucleic acid sequence SEQ ID NO: 1, or a fragment of this sequence, for example with the nucleic acid sequence SEQ ID NO: 12 or 14 or a fragment of these sequences, and which is capable of interfering with the interaction between the PAP1 protein, or a homolog thereof, and parkin. "Modification of genetic and/or chemical nature" can mean any mutation, substitution, deletion, addition and/or modification of one or more residues. The term "derivative" also comprises the sequences which are homologous to the sequence under consideration, which are derived from other cellular sources and in particular cells of human origin, or from other organisms, and which possess an activity of the same type. Such homologous sequences can be obtained by hybridization experiments. The hybridizations can be carried out with nucleic acid libraries, using the native sequence or a fragment of this sequence as probe, under varied conditions of hybridization (Maniatis et al., 1989). Moreover, the term "fragment" or "part" refers to any portion of the molecule under consideration, which comprises at least 5 consecutive residues, preferably at least 9 consecutive residues, even more preferably at least 15 consecutive residues. Typical fragments can comprise at least 25 consecutive residues.

Such derivatives or fragments can be generated with different aims, such as in particular that of increasing their therapeutic effectiveness or of reducing their side effects, or that of conferring novel pharmacokinetic and/or biological properties thereon.

As a peptide which is derived from the PAP1 protein and from the homologous forms, mention may be made in particular of any peptide which is capable of interacting with parkin, but which bears an effector region which has been made nonfunctional. Such peptides can be obtained by deletion, mutation or disruption of this effector region on the PAP1 protein and homologous forms. Such modifications can be carried out for example by in vitro mutagenesis, by introducing additional elements or synthetic sequences, or by deletions or substitutions of the original elements. When such a derivative as defined above is prepared, its activity as partial inhibitor of the binding of the PAP1 protein, and of the homologous forms on its binding site on parkin, can be demonstrated. Any technique known to one skilled in the art can of course be used for this purpose.

They can also be fragments of the sequences indicated above. Such fragments can be generated in various ways. In particular they can be synthesized chemically, on the basis of the sequences given in the present application, using the peptide synthesizers known to one skilled in the art. They can also be synthesized genetically, by expression in a host cell of a nucleotide sequence which encodes the desired peptide. In this case, the nucleotide sequence can be prepared chemically using an oligonucleotide synthesizer, on the basis of the peptide sequence given in the present application and of the genetic code. The nucleotide sequence can also be prepared from sequences given in the present application, by enzymatic cleavage, ligation, cloning, etc., according to the techniques known to one skilled in the art, or by screening DNA libraries with probes which are developed from these sequences.

Moreover, the peptides of the invention, i.e., which are capable of modulating, at least partially, the interaction between the PAP1 protein, and homologous forms, and parkin, can also be peptides which have a sequence corresponding to the site of interaction of the PAP1 protein and of the homologous forms on parkin.

Other peptides according to the invention are peptides which are capable of competing with the peptides defined above for the interaction with their cellular target. Such peptides can be synthesized in particular on the basis of the sequence of the peptide under consideration, and their capacity for competing with the peptides defined above can be determined.

A specific subject of the present invention relates to the PAP1 protein. It is more particularly the PAP1 protein comprising the sequence SEQ ID NO: 2 or a fragment or derivative of this sequence, for example the PAP1 protein, sequences SEQ ID NO: 13 or 15 or fragments of these sequences.

Another subject of the invention lies in polyclonal or monoclonal antibodies or antibody fragments or derivatives, which are directed against a polypeptide as defined above. Such antibodies can be generated by methods known to one skilled in the art. In particular, these antibodies can be prepared by immunizing an animal against a peptide compound of the invention (in particular a polypeptide or a peptide comprising all or part of the sequence SEQ ID NO: 2), sampling the blood and isolating the antibodies. These antibodies can also be generated by preparing hybridomas according to the techniques known to one skilled in the art.

More preferably, the antibodies or antibody fragments of the invention have the capacity to modulate, at least partially, the interaction of the claimed peptides with parkin.

Moreover, these antibodies can also be used for detecting and/or assaying the expression of PAP1 in biological samples and, consequently, for providing information on its activation state.

The antibody fragments or derivatives are for example Fab or Fab'2 fragments, single-chain antibodies (ScFv), etc. They are in particular any fragment or derivative which retains the antigenic specificity of the antibodies from which they are derived.

The antibodies according to the invention are more preferably capable of binding the PAP1 proteins which comprise the sequence SEQ ID NO: 2 or 13 in particular the region of this protein which is involved in the interaction with parkin. These antibodies (or fragments or derivatives) are more preferably capable of binding an epitope which is present in the sequence between residues 1 and 344 of the sequence SEQ ID NO: 2.

The invention also relates to compounds which are not peptide or not exclusively peptide, which can be used as a pharmaceutical agent. It is in fact possible, from the active protein motifs described in the present application, to prepare molecules which are modulators of the activity of PAP1, are not exclusively peptide, and are compatible with pharmaceutical use, in particular by duplicating the active motifs of the peptides with a structure which is not a peptide, or which is not of exclusively peptide nature.

A subject of the present invention is also any nucleic acid which encodes a peptide compound according to the invention. It can be, in particular, a nucleic acid comprising all or part of the sequence which is presented in SEQ ID NO: 1, 12 or 14 or a derivative thereof. For the purposes of the present invention, "derived sequence" is intended to mean any sequence which hybridizes with the sequence which is presented in SEQ ID NO: 1, or with a fragment of this sequence, and which encodes a peptide compound according to the invention, as well as the sequences which result from the latter by degeneracy of the genetic code. For example, nucleic acids according to the invention comprise all or part of the nucleic sequence SEQ ID NO: 12 or 14.

Moreover, the present invention relates to sequences which have a significant percentage of identity with the sequence presented in SEQ ID NO: 1 or with a fragment thereof and which encodes a peptide compound with physiological behavior which is comparable to that of the PAP1 protein. "Significant percentage of identity" is intended to mean a percentage of at least 60%, preferably 80%, more preferably 90% and even more preferably 95%.

The various nucleotide sequences of the invention may or may not be of artificial origin. They can be genomic, cDNA or RNA sequences, hybrid sequences or synthetic or semi-synthetic sequences. These sequences can be obtained either by screening DNA libraries (cDNA library, genomic DNA library), by chemical synthesis, by mixed methods which include the chemical or enzymatic modification of sequences which are obtained by screening of libraries, or by searching for homology in nucleic acid or protein databases. The abovementioned hybridization is preferably carried out under the conditions described by Sambrook et al. (1989, pages 9.52-9.55). It is advantageously carried out under highly stringent hybridization conditions. For the purposes of the present invention, "highly stringent hybridization conditions" is intended to mean the following conditions:

1—Competition of the membranes and PRE-HYBRIDIZATION:
Mix: 40 µl salmon sperm DNA (10 mg/ml)
+40 µl human placenta DNA (10 mg/ml)
Denature for 5 min. at 96° C., then immerse the mixture in ice.
Remove the SSC 2× buffer and pour 4 ml formamide mix into the hybridization tube which contains the membranes.
Add the mixture of the two denatured DNAs.
Incubate at 42° C. for 5 to 6 hours, with rotation.

2—Competition of the labeled probe:
Add to the labeled and purified probe 10 to 50 µl Cot I DNA, according to the quantity of non-specific hybridizations.
Denature 7 to 10 min. at 95° C.
Incubate at 65° C. for 2 to 5 hours.

3—Hybridization:
Remove the pre-hybridization mix
Mix 40 µl salmon sperm DNA+40 µl human placenta DNA;
denature 5 min. at 96° C., then immerse in ice.
Add to the hybridization tube 4 ml formamide mix, the mixture of the two DNAs and the labeled probe/denatured Cot I DNA.
Incubate 15 to 20 hours at 42° C., with rotation.

4—Washes:
One wash at room temperature in SSC 2×, to rinse.
2 times 5 minutes at room temperature SSC 2× and SDS 0.1%.
2 times 15 minutes SSC 0.1× and SDS 0.1% at 65° C.
Wrap membranes in Saran and expose.

The hybridization conditions described above are suitable for hybridization under highly stringent conditions of a nucleic acid molecule varying in length from nucleotides to several hundred nucleotides.

The hybridization conditions described above could of course be adjusted to take into account the length of the nucleic acid for which hybridization is desired or the type of label chosen, according to techniques known to one skilled in the art.

For example, the suitable hybridization conditions can be adjusted according to the teachings contained in the work of Hames and Higgins (1985) (Nucleic Acid Hybridization a Practical Approach, Hames and Higgins Ed., IRL Press, Oxford) or, alternatively, in the work of F. Ausubel et al (1999) (Current Protocols in Molecular Biology, Green Publishing Associates and Wiley Interscience, NY).

For the purposes of the invention, a particular nucleic acid encodes a polypeptide comprising the sequence SEQ ID NO: 2 or a fragment or derivative of this sequence, in particular the human PAP1 protein. It is advantageously a nucleic acid comprising the sequence SEQ ID NO: 1, 12 or 14.

Such nucleic acids can be used for producing the peptide compounds of the invention. The present application thus relates to a method for preparing such peptide compounds, according to which a cell which contains a nucleic acid according to the invention is cultured under conditions for expressing said nucleic acid, and the peptide compound produced is recovered. In this case, the portion which encodes said peptide compound is generally placed under the control of signals which allow its expression in a host cell. The choice of these signals (promoters, terminators, secretion leader sequence, etc.) can vary as a function of the host cell used. Moreover, the nucleic acids of the invention can form part of a vector which can replicate autonomously or can integrate. More particularly, autonomously-replicating vectors can be prepared using sequences which replicate autonomously in the chosen host. As regards the integrating vectors, they can be prepared for example using sequences which are homologous to certain regions of the genome of the host, which allow, by homologous recombination, the integration of the vector. It can be a vector of plasmid, episomal, chromosomal, viral etc., type.

The host cells which can be used for producing the peptide compounds of the invention via the recombinant pathway are both eukaryotic and prokaryotic hosts. Among the eukaryotic hosts which are suitable, mention may be made of animal cells, yeasts or fungi. In particular, as regards yeasts, mention may be made of the yeasts of the genus *Saccharomyces*, *Kluyveromyces*, *Pichia*, *Schwanniomyces*, or *Hansenula*. As regards animal cells, mention may be made of COS, CHO, C127, PC12 etc., cells. Among the fungi, mention may be made more particularly of *Aspergillus* ssp. or *Trichoderma* ssp. As prokaryotic hosts, use of the following bacteria is preferred: *E. coli, Bacillus* or *Streptomyces*.

A subject of the present invention is also non-human mammals comprising in their cells a nucleic acid or vector according to the invention.

Such mammals (rodents, canines, rabbits, etc.) can be used in particular to study the properties of PAP1 and identify compounds with therapeutic aims. The genome of such a transgenic animal can be modified by knock-in or knock-out alteration or modification of one or more genes. This modification can be carried out using conventional alterative or mutagenic agents, or via directed mutagenesis. Modification of the genome can also be the result of the insertion of a gene(s) or the replacement of a gene(s) in its (their) wild or mutated form. Genome modifications are advantageously carried out on reproductive stem cells and advantageously on pronuclei. Transgenesis can be performed by microinjection of an expression cassette comprising the modified genes in the two fertile pronuclei. Thus an animal according to the present invention can be obtained by injection of an expression cassette comprising a nucleic acid. Preferably, this nucleic acid is a DNA which can be a genomic DNA (gDNA) or a complementary DNA (cDNA). The construction of transgenic animals according to the invention can be carried out according to conventional techniques well known to one skilled in the art. A person skilled in the art can in particular refer to the production of transgenic animals, and specifically to the production of transgenic mice, as described in the following U.S. Pat. No. 4,873,191; U.S. Pat. No. 5,464,764 and U.S. Pat. No. 5,789,215; the contents of these documents are incorporated herein by reference.

In short, a polynucleotide construct which comprises a nucleic acid according to the invention is inserted into an ES-type stem cell line. Insertion of the polynucleotide construct is preferably performed by electroporation, as described by Thomas et al. (1987, Cell, Vol. 51; 503-512).

The cells which have been subjected to the electroporation step are then screened for the presence of the polynucleotide construct (for example by selection, using markers, or alternatively by PCR or by Southern-type DNA gel electrophoresis analysis) so as to select the positive cells which integrated the exogenous polynucleotide construct into their genome, if necessary after a homologous recombination event. Such a technique is described by Mansour et al, for example. (*Nature* (1988) 336: 348-352).

The positively selected cells are then isolated, cloned and injected into 3.5 day-old mouse blastocysts, as described by Bradley (1987, *Production and Analysis of Chimaeric Mice*. In: E. J. Robertson (Ed., Teratocarcinomas and Embryonic Stem Cells: A Practical Approach, IRL Press. Oxford, page 113)). Blastocysts are then introduced into a female animal host and development of the embryo is pursued to full term.

Alternatively, positively selected ES-type cells are placed in contact with 2.5 day-old embryos at an 8-16 cell stage (morulae), as described by Wood et al. (1993. Proc. Natl. Acad. Sci. USA, vol. 90: 4582-4585) or by Nagy et al. (1993. Proc. Natl. Acad. Sci. USA, vol. 90: 8424-8428). The ES cells are internalized in order to extensively colonize the blastocyst, including the cells which produce the germ line.

The descendants are then tested to determine those which have integrated the polynucleotide construct (the transgene).

The nucleic acids according to the invention can also be used to prepare genetic antisense or antisense oligonucleotides which can be used as pharmaceutical agents. Antisense sequences are oligonucleotides of short length, which are complementary to the coding strand of a given gene, and consequently are capable of specifically hybridizing with the mRNA transcript, which inhibits its translation into a protein. A subject of the invention is thus antisense sequences which are capable of inhibiting, at least partially, the interaction of the PAP1 proteins on parkin. Such sequences can consist of all or part of the nucleic acid sequences defined above. They are generally sequences, or fragments of sequences, which are complementary to sequences encoding peptides which interact with parkin. Such oligonucleotides can be obtained by fragmentation, etc., or by chemical synthesis.

The claimed sequences can be used in the context of gene therapies, for transferring and expressing, in vivo, antisense sequences or peptides which are capable of modulating the interaction of the PAP1 protein with parkin. In this respect, the sequences can be incorporated in viral or nonviral vectors, which allows their administration in vivo (Kahn et al., 1991). As viral vectors in accordance with the invention, mention may be made most particularly of adenivorus, retrovirus, adeno-associated virus (AAV) or herpes virus type vectors. A subject of the present application is also recombination-defective viruses comprising a nucleic acid which encodes a polypeptide according to the invention, in particular a polypeptide or peptide comprising all or part of the sequence SEQ ID NO: 2 or of a derivative of this sequence, for example all or part of the sequence SEQ ID NO: 12 or 14 or derivatives of these sequences.

The invention also enables the preparation of nucleotide probes, which may or may not be synthetic, and which are capable of hybridizing with the nucleotide sequences defined above or their complementary strand. Such probes can be used in vitro as a diagnostic tool for detecting the expression or overexpression of PAP1, or alternatively for revealing genetic abnormalities (incorrect splicing, polymorphism, point mutations, etc.). These probes can also be used for detecting and isolating homologous nucleic acid sequences which encode peptides as defined above, from other cellular sources and preferably from cells of human origin. The probes of the invention generally comprise at least 10 bases, and they can for example comprise up to the whole of one of the abovementioned sequences or of their complementary strand. Preferably, these probes are labeled prior to their use. For this, various techniques known to one skilled in the art can be employed (radioactive, fluorescent, enzymatic, chemical labeling, etc.).

The invention also relates to primers or primer pairs which make it possible to amplify all or part of a nucleic acid encoding a PAP1, for example a sequence primer chosen from among SEQ ID NO: 16-41.

A subject of the invention is also any pharmaceutical composition which comprises, as an active agent, at least one compound as defined above, in particular a peptide compound.

A subject of the invention is in particular any pharmaceutical composition which comprises, as an active agent, at least one antibody and/or one antibody fragment as defined above, as well as any pharmaceutical composition which comprises, as an active agent at least one nucleic acid or one vector as defined above.

A subject of the invention is also any pharmaceutical composition which comprises, as an active agent, a chemical molecule which is capable of increasing or of decreasing the interaction between the PAP1 protein and parkin.

Moreover, a subject of the invention is also pharmaceutical compositions in which the peptides, antibodies, chemical molecules and nucleotide sequences defined above are combined mutually or with other active agents.

The pharmaceutical compositions according to the invention can be used for modulating the activity of the parkin protein, and consequently for maintaining the survival of the dopaminergic neurons. More particularly, these pharmaceutical compositions are intended for modulating the interaction between the PAP1 protein and parkin. They are, more preferably, pharmaceutical compositions which are intended for treating diseases of the central nervous system, such as for example Parkinson's disease.

A subject of the invention is also the use of the molecules described above for modulating the activity of parkin or for the typing of diseases of the central nervous system. In particular, the invention relates to the use of these molecules for modulating, at least partially, the activity of parkin.

The invention also relates to a method for screening or characterizing molecules which act on the function of parkin, to include selecting molecules which are capable of binding the sequence SEQ ID NO: 2 or the sequence SEQ ID NO: 4, or a fragment (or derivative) of these sequences. The method comprises, advantageously, bringing the molecule(s) to be tested into contact, in vitro, with a polypeptide which comprises the sequence SEQ ID NO: 2 or the sequence SEQ ID NO: 4, or a fragment (or derivative) of these sequences, and selecting molecules which are capable of binding the sequence SEQ ID NO: 2 (in particular the region between residues 1 and 344) or the sequence SEQ ID NO: 4. The molecules tested can be varied in nature (peptide, nucleic acid, lipid, sugar, etc., or mixtures of such molecules, for example combinatory libraries, etc.). As indicated above, the molecules thus identified can be used for modulating the activity of the parkin protein, and represent potential therapeutic agents for treating neurodegenerative pathologies.

Other advantages of the present invention will appear upon reading the following examples and figure, which should be considered as illustrative and nonlimiting.

LEGENDS TO THE FIGURES

The patent application file contains at least one figure executed in color. Copies of this patent or patent application publication with color figures will be provided by the Office upon request and payment of the necessary fee.

FIG. 1: Representation of the vector pLex9-parkin (135-290)

Figure 2:
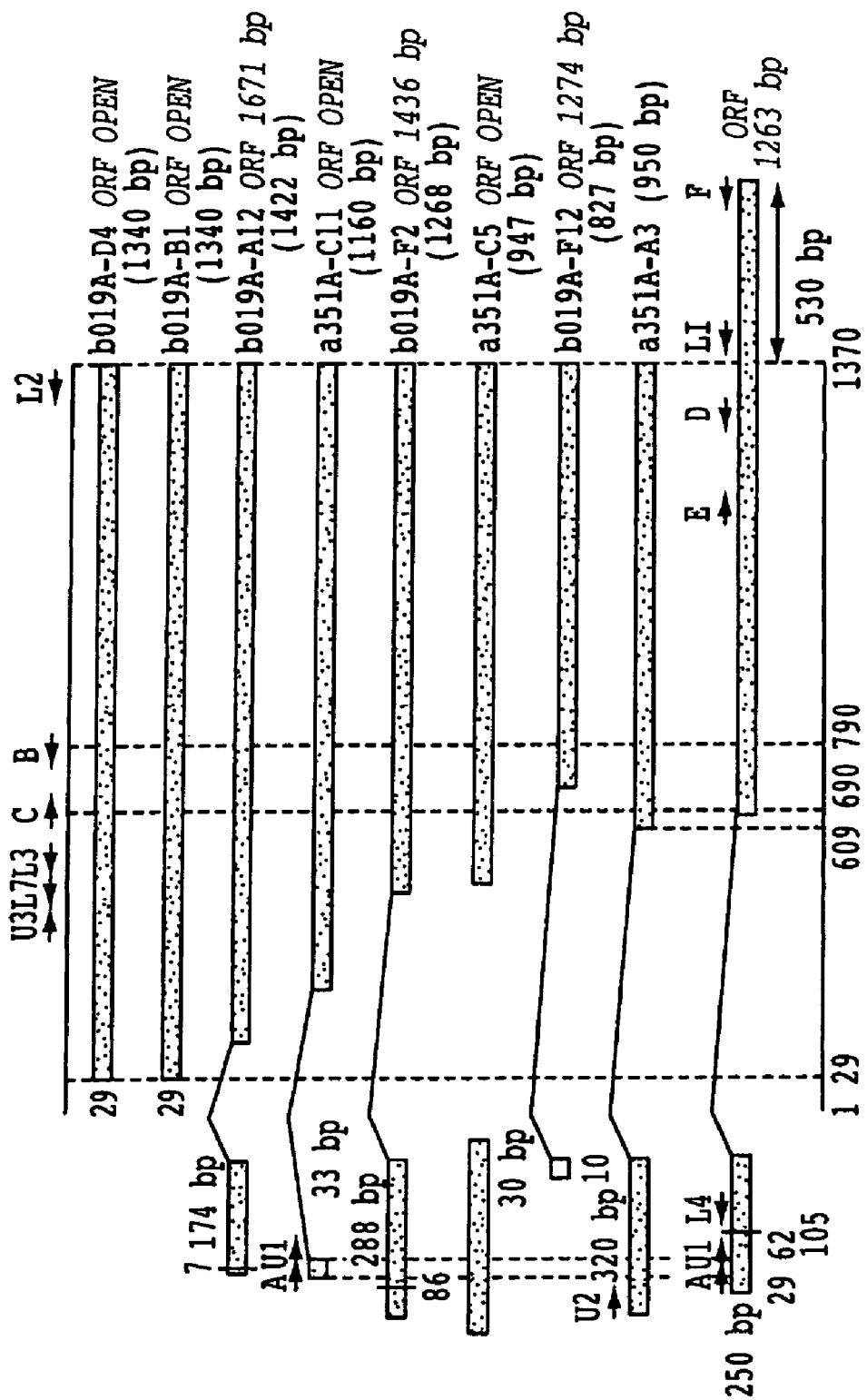

FIG. 2: Results of the first 5'-RACE experiment. 8 clones were obtained. The initial sequence is indicated on the lower part of the figure.

Figure 3:
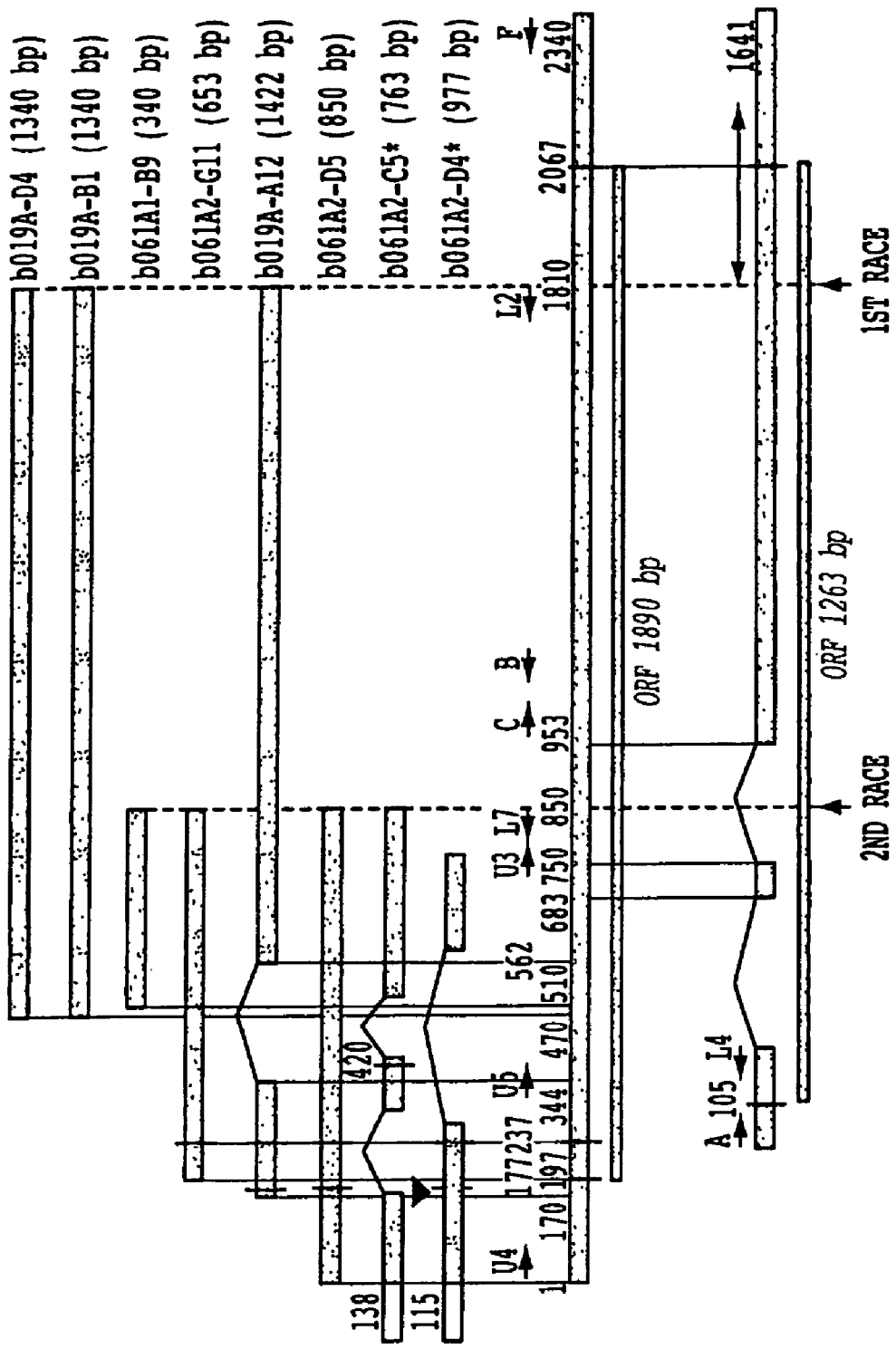

FIG. 3: Results of the second 5'-RACE experiment. Only two of the 8 clones obtained in the first experiment were validated (clones A12 and D5). The initial electronic sequence is indicated 0 the figure. The complete sequence of DNAs and proteins is provided in Sequences 12-15 (SEQ ID NO: 12-15).

Figure 4:
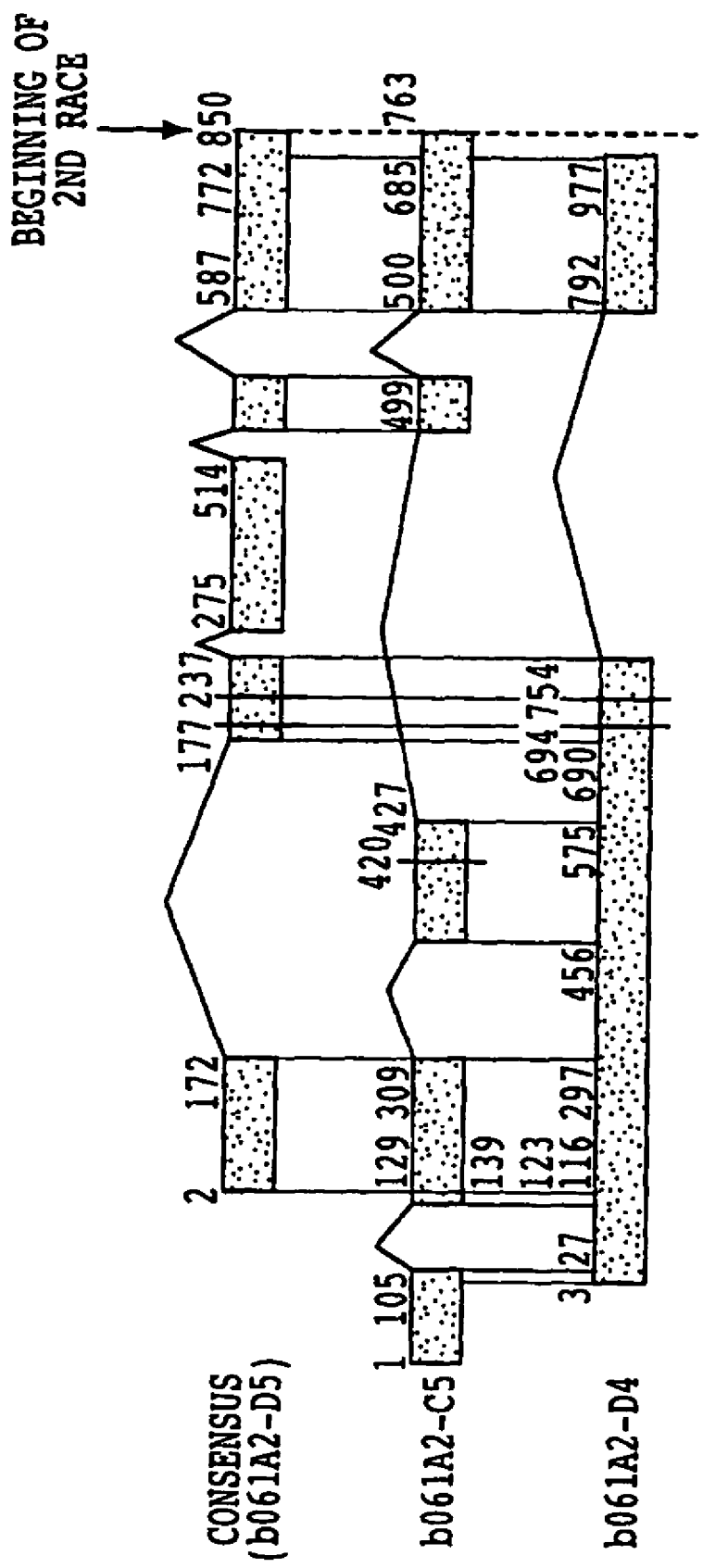

FIG. 4: Detailed view of the organization of clones C5 and D4 from the second 5'-RACE experiment. The resulting consensus sequence is indicated on the upper part of the figure.

Figure 5:
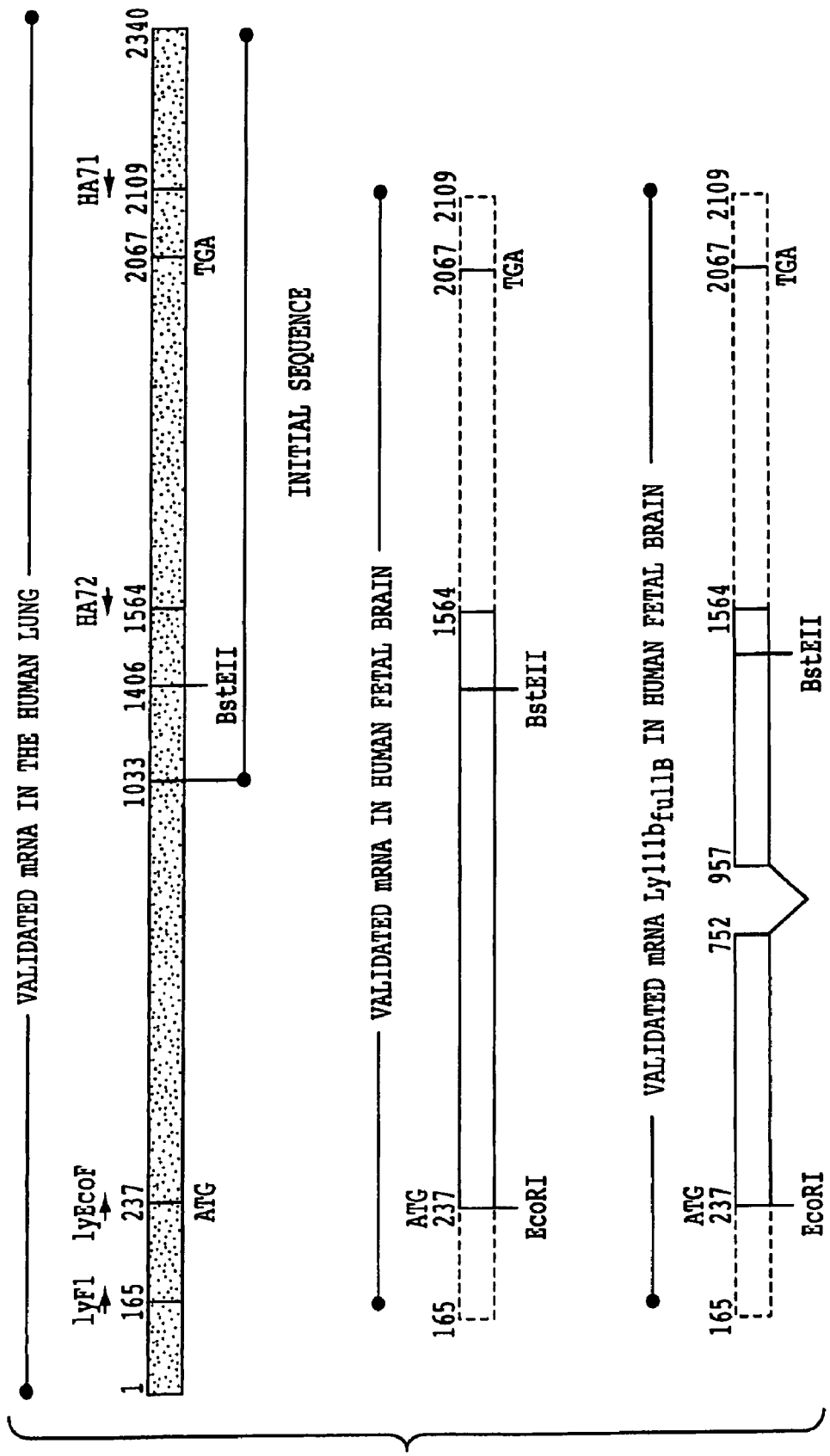

FIG. 5: Structure of transcripts isolated from human brain.

FIG. 6: LY111 (full length) nucleic acid (SEQ ID NO: 47) and protein (SEQ ID NO: 48) sequence from human brain. Double underlined: cysteines retained from domain in zinc finger. Bold: Domain $C_21$. Italic: domain $C_22$.

FIG. 7: LY111 (short version) nucleic acid (SEQ ID NO: 49) and protein (SEQ ID NO: 50) sequence from human brain. Double underlined: cysteines retained from domain in zinc finger. Bold: Domain $C_21$. Italic: domain $C_22$.

Figure 8:
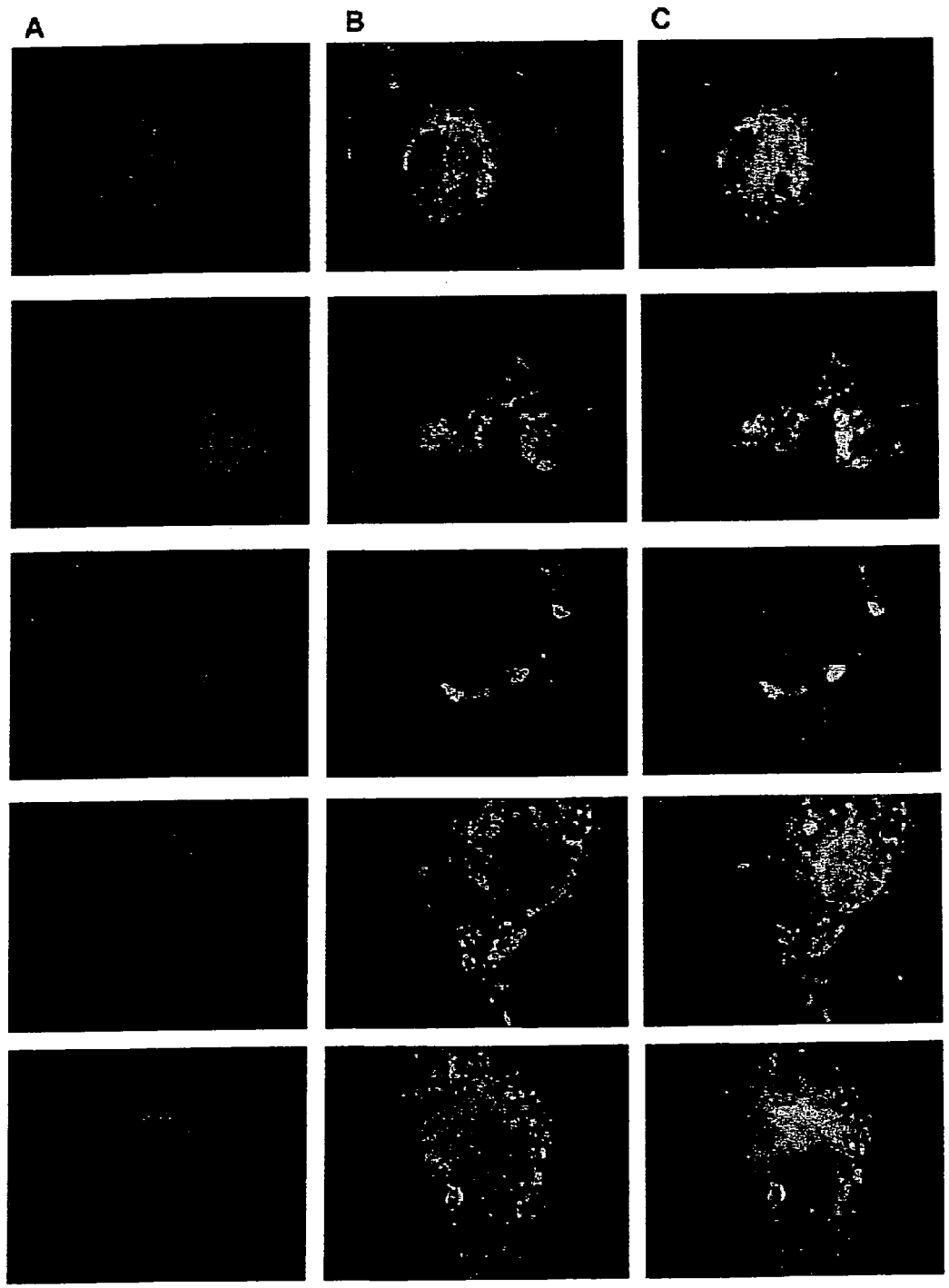
Figure 8B:
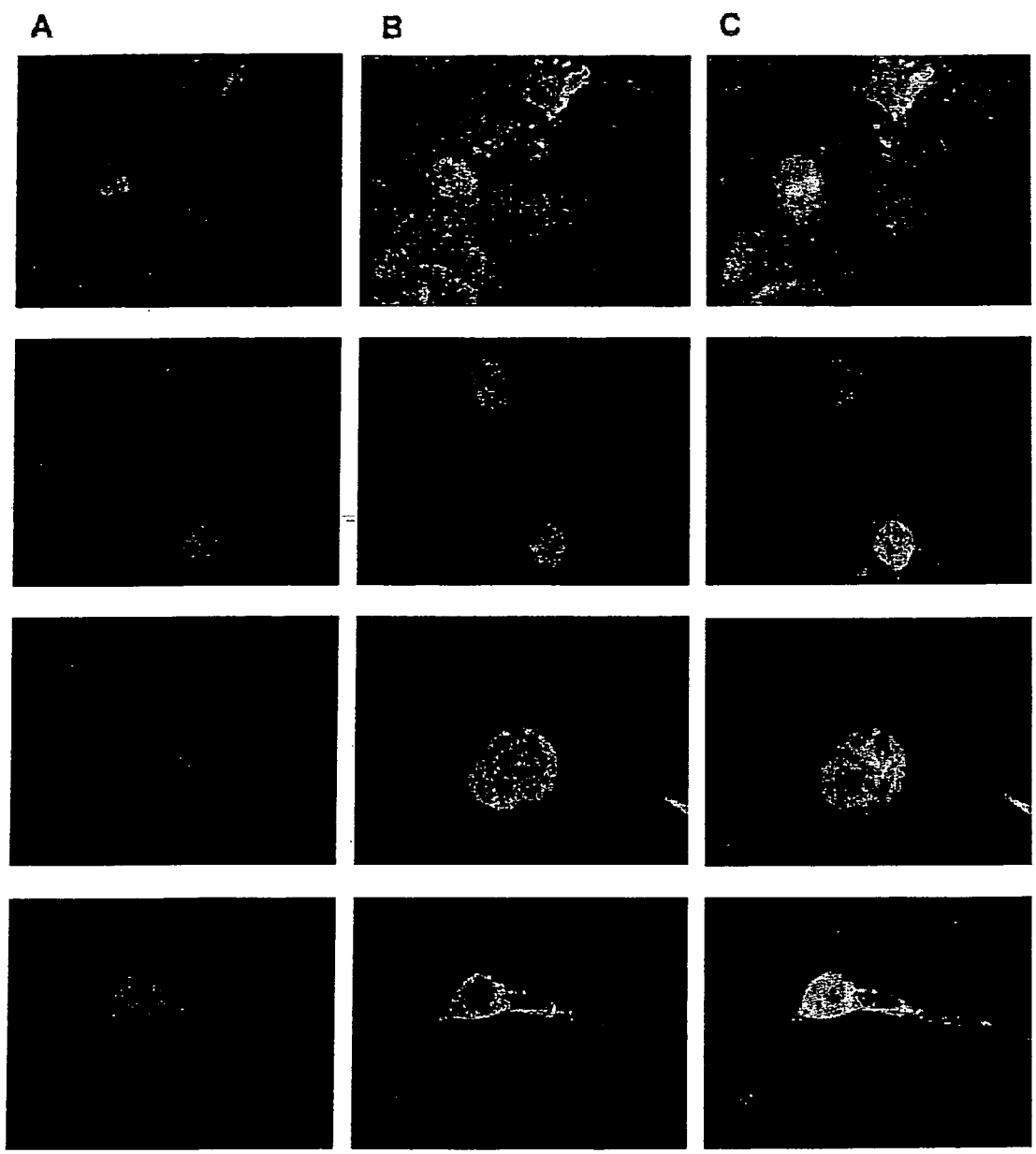

FIG. 8: Location of short (8b) or full length (8a) LY111 protein after expression in Cos-7 cells.

FIG. 9: LY111 (full length) nucleic acid (SEQ ID NO: 12 or 42) and protein (SEQ ID NO: 12 or 43) sequence from human lung.

FIG. 10: LY111 (short version) nucleic acid (SEQ ID NO: 14 or 44) and protein (SEQ ID NO: 15 or 45) sequence from human brain.

MATERIALS AND TECHNIQUES USED

1) Yeast Strains:

Strain L40 of the genus *S. cerevisiae* (Mata, his3D200, trp1-901, leu2-3, 112, ade2, LYS2::(exAop)$_4$-HIS3, URA3::(1exAop)$_8$-Lac4 GAL4, GAL80) was used to verify the protein-protein interactions when one of the protein partners is fused to the LexA protein. The LexA protein is capable of recognizing the LexA response element, which controls the expression of the reporter genes LacZ and His3.

It was cultured on the following culture media:
Complete YPD medium:
   Yeast extract (10 g/l) (Difco)
   Bactopeptone (20 g/l) (Difco)
   Glucose (20 g/l) (Merck)
This medium was solidified by addition of 20 g/l of agar (Difco).
Minimum YNB medium:
   Yeast Nitrogen Base (without amino acids) (6.7 g/l) (Difco)
   Glucose (20 g/l) (Merck)
This medium can be solidified by addition of 20 g/l of agar (Difco). It can also be supplemented with amino acids and/or with 3-amino-1,2,4-triazole by addition of CSM media [CSM-Leu, -Trp, -His (620 mg/l), CSM-Trp (740 mg/l) or CSM-Leu, -Trp (640 mg/l)(Bio101)] and/or of 2.5 mM 3-amino-1,2,4-triazole.

2) Bacterial Strains:

Strain TG1 of *Escherichia coli*, of genotype supE, hsdΔ5, thi, Δ(lac-proAB), F'[tra D36 pro A$^+$B$^+$lacI$^q$ lacZΔM15], was used for constructing plasmids, as a means of amplifying and of isolating recombinant plasmids used. It was cultured on the following medium:
Medium LB:
   NaCl (5 g/l) (Prolabo)
   Bactotryptone (10 g/l) (Difco)
   Yeast extract (5 g/l) (Difco)
This medium is solidified by addition of 15 g/l of agar (Difco).

Ampicillin was used at 100 µg/ml; this antibiotic is used to select the bacteria, which have received the plasmids bearing the gene for resistance to this antibiotic, as a marker.

Strain HB101 of *Escherichia coli* of genotype supE44, ara 14, galK2, lacY1, Δ(gpt-proA)62, rpsL20(Str$^r$), xyl-5, mtl-1, recA13, Δ(mcrC-mrr), HsdS$^-$(r$^-$m$^-$) was used as means for amplifying and isolating plasmids which originate from the human lymphocyte cDNA library. It was cultured on
Medium M9:
   Na$_2$HPO$_4$ (7 g/l) (Prolabo)
   KH$_2$PO$_4$ (3 g/l) (Prolabo)
   NH4Cl (1 g/l) (Prolabo)
   NaCl (0.5 g/l) (Prolabo)
   Glucose (20 g/l) (Sigma)
   MgSO$_4$ (1 mM) (Prolabo)
   Thiamine (0.001%) (Sigma)
This medium is solidified by addition of 15 g/l of agar (Difco). Leucine (50 mg/l) (Sigma) and proline (50 mg/l) (Sigma) should be added to the M9 medium to enable the growth of strain HB101.

During the selection of plasmids which originate from the lymphocyte cDNA two-hybrid library, leucine was not added to the medium because the plasmids bear a Leu2 selection marker.

3) Plasmids:

The 5-kb vector pLex9 (pBTM116) (Bartel et al., 1993), which is homologous to pGBT10 and which contains a multiple cloning site located downstream of the sequence which encodes the LexA bacterial repressor, and upstream of a terminator, for forming a fusion protein.

pLex-HaRasVal12; plasmid pLex9, as described in application WO 98/21327, which contains the sequence encoding the HaRas protein mutated at position Val12, which is known to interact with the mammalian Raf protein (Vojtek et al., 1993). This plasmid was used to test the specificity of interaction of the PAP1 protein in strain L40.

pLex9-cAPP; plasmid pLex9 which contains the sequence encoding the cytoplasmic domain of the APP protein, known to interact with the PTB2 domain of FE65. This plasmid was used to test the specificity of interaction of the PAP1 protein in strain L40.

4) Synthetic Oligonucleotides:

TTAAGAATTC GGAAGTCCAG CAGGTAG    (SEQ ID No 5)

ATTAGGATCC CTACACACAA GGCAGGGAG  (SEQ ID No 6)

Oligonucleotides which made it possible to obtain the PCR fragment which corresponds to the central region of parkin, bordered by the EcoRI and BamHI sites.

```
GCGTTTGGAA TCACTACAG            (SEQ ID No 7)

GGTCTCGGTG TGGCATC              (SEQ ID No 8)

CCGCTTGCTT GGAGGAAC             (SEQ ID No 9)

CGTATTTCTC CGCCTTGG             (SEQ ID No 10)

AATAGCTCGA GTCAGTGCAG GACAAGAG  (SEQ ID No 11)
```

Oligonucleotides which were used to sequence the insert corresponding to the PAP1 gene.

The oligonucleotides are synthesized using an Applied System ABI 394-08 machine. They are removed from the synthesis matrix with ammonia and precipitated twice with 10 volumes of n-butanol, and then taken up in water. The quantification is carried out by measuring the optical density (1 $OD_{260}$ corresponds to 30 µg/ml).

5) Preparation of Plasmid DNAs

The preparations of plasmid DNA were carried out according to the protocols recommended by Quiagen, the manufacturer of the DNA purification kits, in small and large amounts:

Quiaprep Spin Miniprep kit, reference: 27106
Quiaprep Plasmid Maxiprep kit, reference: 12613.

6) Enzymatic Amplification of DNA by PCR (Polymerase Chain Reaction):

The PCR reactions are carried out in a final volume of 100 µl in the presence of the DNA matrix, of dNTP (0.2 mM), of PCR buffer (10 mM Tris-HCl pH 8.5, 1 mM $MgCl_2$, 5 mM KCl, 0.01% gelatin), of 10 to 20 pmol of each one of the oligonucleotides and of 2.5 IU of Ampli Taq DNA polymerase (Perkin Elmer). The mixture is covered with 2 drops of liquid petroleum jelly to limit the evaporation of the sample. The machine used is the "Crocodile II" by Appligene.

We used a matrix denaturation temperature of 94° C., a hybridization temperature of 52° C. and a temperature for elongation by the enzyme at 72° C.

7) Ligations:

All the ligation reactions are carried out at 37° C. for one hour in a final volume of 20 µl, in the presence of 100 to 200 µg of vector, 0.1 to 0.5 µg of insert, 40 IU of T4 DNA ligase enzyme (Biolabs) and a ligation buffer (50 mM Tris-HCl pH 7.8; 10 mM $MgCl_2$; 10 mM DTT; 1 mM ATP). The negative control consists of ligating the vector in the absence of insert.

8) Transformation of Bacteria:

The transformation of bacteria with a plasmid is carried out according to the following protocol: 10 µl of the ligation volume are used to transform the TG1 bacteria, according to the method of Chung (Chung et al., 1989). After transformation, the bacteria are placed on an LB medium+ampicillin and incubated for 16 h at 37° C.

9) Separation and Extraction of DNAs:

The separation of DNAs is carried out as a function of their size, on agarose gel by electrophoresis according to Maniatis (Maniatis et al., 1989): 1% agarose gel (Gibco BRL) in a TBE buffer (90 mM Tris base; 90 mM borate; 2 mM EDTA).

10) Fluorescent Sequencing of Plasmid DNAs:

The sequencing technique used is derived from the method of Sanger (Sanger et al., 1977) and adapted for sequencing by fluorescence, which is developed by Applied Biosystems. The protocol used is that described by the designers of the system (Perkin Elmer, 1997).

11) Transformation of Yeast:

The plasmids are introduced into the yeast using a conventional technique for transforming yeast developed by Gietz (Gietz et al., 1992) and modified in the following way:

In the specific case of the transformation of yeast with the lymphocyte cDNA library, the yeast used contains the plasmid pLex9-parkin (135-290), which encodes the central portion of parkin fused to the LexA protein. It is cultured in 200 ml of YNB minimum medium, supplemented with amino acids CSM-Trp, at 30° C. with shaking until a density of $10^7$ cells/ml is attained. To carry out the transformation of the yeasts, according to the above protocol, the cell suspension was separated into 10 50-µl tubes, into which 5 µg of the library were added. Heat shock was carried out for 20 minutes, and the cells were collected by centrifugation and resuspended in 100 ml of YPD medium for 1 h at 30° C., and in 100 ml of YNB medium, supplemented with CSM-Leu, -Trp, for 3 h 30 at 30° C. The efficiency of the transformation is determined by placing various dilutions of transformed cells on solid YNB medium which is supplemented with CSM-Trp, -Leu. After 3 days of culture at 30° C., the colonies obtained were counted, and the rate of transformation per µg of lymphocyte library DNA was determined.

12) Isolation of Plasmids Extracted from Yeast:

5 ml of a yeast culture, which is incubated for 16 h at 30° C., are centrifuged, and taken up in 200 µl of a lysis buffer (1M Sorbitol, 0.1 M $KH_2PO_4/K_2HPO_4$ pH 7.4, 12.5 mg/ml zymolyase) and incubated for 1 h at 37° C. The lysate is then treated according to the protocol recommended by Quiagen, the manufacturer of the DNA purification kit, Quiaprep Spin Miniprep kit, ref 27106.

13) β-Galactosidase Activity Assay:

A sheet of nitrocellulose is preplaced on the Petri dish containing the yeast clones, which are separated from each other. This sheet is then immersed in liquid nitrogen for 30 seconds, in order to rupture the yeasts and thus to release the β-galactosidase activity. After thawing, the sheet of nitrocellulose is placed, colonies facing upwards, in another Petri dish containing a Whatman paper which has been presoaked in 1.5 ml of PBS solution (60 mM $Na_2HPO_4$, 40 mM $NaH_2PO_4$, 10 mM KCl, 1 mM $MgSO_4$, pH 7) containing 15 µl of X-Gal (5-bromo-4-chloro-3-indoyl-β-D-galactoside) at 40 mg/ml of N,N-dimethylformamide. The dish is then placed in an incubator at 37° C. The assay is termed positive when the colonies on the membrane turn blue after 12 hours.

Example 1

Construction of a Vector Which Allows the Expression of a Fusion Protein in which Fusion is Between the Central Portion of Parkin and the Lexa Bacterial Repressor Screening a library using the double-hybrid system requires the central region of parkin to be fused to a DNA binding protein, such as the LexA bacterial repressor. The expression of this fusion protein is carried out using the vector pLex9 (cf. materials and methods), into which the sequence encoding the central region of parkin, which is in the sequence presented in sequence SEQ ID NO: 3 or 4, is introduced, in the same reading frame as the sequence corresponding to the LexA protein.

The 468 bp-fragment of DNA corresponding to the 156 amino acids of the central region of parkin (SEQ ID NO: 4), which begins at amino acid 135, was obtained by PCR using the oligonucleotides (sequence SEQ ID NO: 5 and NO: 6), which also made it possible to introduce the EcoRI site at the 5' end and a stop codon and a BamHI site at the 3' end. The PCR fragment was introduced between the EcoRI and BamHI sites of the multiple cloning site of the plasmid pLex9, downstream of the sequence encoding the protein LexA, in order to produce the vector pLex9-parkin (135-290) (FIG. 1).

The construct was verified by sequencing the DNA. This verification made it possible to show that this fragment does not have mutations generated during the PCR reaction, and that it was fused in the same open reading frame as that of the fragment corresponding to LexA.

Example 2

Screening a Lymphocyte Fusion Library

We used the double-hybrid method (Fields and Song, 1989).

Screening a fusion library makes it possible to identify clones producing proteins which are fused to the transactivating domain of GAL4, and which are able to interact with the protein of interest described in Example 1 (central region of parkin). This interaction makes it possible to reconstitute a transactivator which will then be capable of inducing the expression of the reporter genes His3 and LacZ in strain L40.

To carry out this screening we chose a fusion library which is prepared from cDNA originating from peripheral human lymphocytes, supplied by Richard Benarous (Peytavi et al., 1999). Yeasts were transformed with the lymphocyte library and positive clones were selected as described below.

During screening, it is necessary to maintain the probability that each separate plasmid from the fusion library is present in at least one yeast at the same time as the plasmid pLex9-parkin (135-290). To maintain this probability, it is important to have a good efficiency of transformation of the yeast. For this, we chose a protocol for transforming yeast which gives an efficiency of $2.6 \times 10^5$ transformed cells per μg of DNA. In addition, as cotransforming yeast with two different plasmids reduces this efficiency, we preferred to use a yeast which is pretransformed with the plasmid pLex9-parkin (135-290). This strain L40 pLex9-parkin (135-290), of phenotype His-, Lys-, Leu-, Ade-, was transformed with 50 μg of plasmid DNA from the fusion library. This amount of DNA enabled us to obtain, after estimation, $1.3 \times 10^7$ transformed cells, which corresponds to a number which is slightly higher than the number of separate plasmids which constitute the library. According to this result, virtually all of the plasmids of the library can be considered to have been used to transform the yeasts. The selection of the transformed cells, which are capable of reconstituting a functional transactivator, was done on a YNB medium which was supplemented with 2.5 mM 3-amino-1,2,4-triazole and 620 mg/l of CSM (Bio101), and which contains no histidine, no leucine and no tryptophan.

At the end of this selection, many clones with a His+ phenotype were obtained. A β-galactosidase activity assay was carried out on these transformants to validate, on the basis of the expression of the other reporter gene, LacZ, this number of obtained clones. 115 clones had the His+, β-Gal+ double phenotype, which can correspond to a protein-protein interaction.

Example 3

Isolation of the Library Plasmids in the Clones Selected

To identify the proteins which are able to interact with the central region of parkin, the fusion library plasmids contained in the yeasts which were selected during the double-hybrid screening were extracted. To be able to obtain a large amount thereof, this isolation calls for a prior transformation of E. coli with an extract of DNA from the positive yeast strains. As the library plasmid which is contained in this extract is a yeast/E. coli shuttle plasmid, it can easily replicate in the bacterium. The library plasmid was selected by complementing the auxotrophic HB101 bacterium for leucine, on leucine-lacking medium.

The plasmid DNAs from the bacterial colonies which are obtained after transformation with extracts of DNA from yeasts were analyzed by digestion with restriction enzymes and separation of the DNA fragments on agarose gel. Among the 115 clones analyzed, one clone containing a library plasmid, which showed a different profile from the others, was obtained. This plasmid, termed pGAD-Ly111b, was studied more precisely.

Example 4

Determination of the Sequence of the Insert Contained in the Plasmid Identified

Sequencing of the insert contained in the plasmid identified was carried out, firstly, using the oligonucleotide SEQ ID NO: 7, which is complementary to the sequence GAL4TA, close to the EcoRI site of insertion of the lymphocyte cDNA library; then, secondly, using the oligonucleotides SEQ ID NO: 8 to SEQ ID NO: 11, which correspond to the sequence of the insert which is obtained during the course of the sequencing. The sequence obtained is presented on the sequence SEQ ID NO: 1. The protein thus identified was referred to as PAP1 (Parkin-Associated Protein 1).

Comparison of the sequence of this insert with the sequences which are contained in the GENBank and EMBL (European Molecular Biology Lab) databases showed a homology of 25% at the protein level with various members of the synaptotagmin family. The synaptotagmins are part of a family of membrane proteins which are encoded by at least eleven different genes, which are expressed in the brain and other tissues. They contain a single transmembrane domain and two calcium-regulated domains which are termed $C_2$. It is in this domain that the homology between the synaptotagmins and the PAP1 protein is found. No other significant homology was observed.

Example 5

Analysis of the Specificity of Interaction Between the Central Region of Parkin and the PAP1 Protein To determine the specificity of interaction between the fragment corresponding to the PAP1 protein and the central region of parkin, a two-hybrid test for specific interaction with other nonrelevant proteins was carried out. To carry out this test, we transformed strain L40 with the control plasmids plex9-cAPP or pLex9-HaRasVal12, in place of the plasmid pLex9-parkin (135-290), which respectively encode the cytoplasmic domain of the APP or the HaRasVal12 protein, which are fused to the LexA DNA binding domain, and with the plasmid isolated during the screening of the two-hybrid library. A β-Gal activity assay was carried out on the cells which were transformed with the various plasmids, to determine a protein-protein interaction. According to the result of the assay, only the yeasts which were transformed with the plasmid which was isolated during the screening of the two-hybrid library, and with the plasmid pLex9-parkin (135-290), had a β-Gal+ activity, which thus shows an interaction between the central region of parkin and the PAP1 protein.

This interaction thus turns out to be specific, since this fragment of PAP1 does not seem to interact with the cAPP or HaRasVal12 proteins.

These results thus show the existence of a novel protein, referred to as PAP1, which is capable of interacting specifically with parkin. This protein, which is related to the synaptotagmins, shows no significant homology with known proteins, and can be used in therapeutic or diagnostic applications, for producing antibodies, probes or peptides, or for screening active molecules.

Example 6

Cloning of the PAP1 Gene from a Human Lung DNA Library

In order to identify the complete sequence of the human PAP1 gene and characterize the existence of variant forms, two elongation approaches were carried out from the sequence SEQ ID NO: 1. Two sequences were thus obtained, of 1644 bp and 1646 bp respectively, comprising an elongation of 330 bp as compared to the sequence SEQ ID NO: 1. Nonetheless, analysis of these sequences showed differences in the consensus region, which were apparent after translation. Thus an ORF of 420aa is obtained in one case and an ORF of 230aa with the other sequence. The protein sequence obtained was compared with the known sequences and revealed a 24% homology over the 293 amino acids that overlap with the human synaptogamin 1 (p65)(p21579). The function of the synaptogamin 1 can be a regulating role in the membrane interactions which occur during the synaptic vesicle traffic in the area of the synapse. The synaptogamin binds the acidic phospholipids with a certain specificity. Moreover, a calcium-dependent interaction between the synaptogamin and the activated kinase C protein receptors was reported. The synaptogamin can also bind three other proteins, which are neurexin, syntaxin and ap2. Given the premature and abrupt disappearance of any homology between the sequences identified and the family of synaptogamins, the sequence identified may contain a deletion as compared to the natural sequence. To verify this hypothesis and validate the sequences, a RT-PCR and sequencing experiment was carried out using the 1644 bp sequence. The sequence obtained comprises an ORF of 420aa with a homology with the synaptogamins on the same order.

In an effort to obtain a larger sequence and verify whether the sequence obtained could correspond to a form of splicing, a 5'-RACE elongation experiment was begun at the 3' region of the validated sequence, using the L1 and L2 oligonucleotides on a human lung cDNA preparation.

The results obtained appear in FIG. 2 and show the identification of 8 clones corresponding to 6 different 5' terminal ends. Three of these contain a stop codon which interrupts the ORF (clones A12, F2, F12) and clone A3 contains no ORF. The presence of various transcripts was confirmed by RT-PCR and nested RT-PCR (Table 1).

TABLE 1

| RT-PCR | Primary | Secondary PCR U3-L3 | Secondary PCR U1-L4 | Secondary PCR C-B |
|---|---|---|---|---|
| U3-L3 | 170 | | | |
| A-L4 | 153 | | + | |
| A-L3 | Smear | + | | |
| U1-L4 | 130 | | | |

TABLE 1-continued

| RT-PCR | Primary | Secondary PCR U3-L3 | Secondary PCR U1-L4 | Secondary PCR C-B |
|---|---|---|---|---|
| U1-L3 | Smear | + | | |
| U1-B | 415 | | | + |
| U2-B | 515 | | | + |
| Expected size | | 170 | 130 | 120 |

The U3-L3 and C-B primer pairs are specific to the common fragment of the sequence, the A and U1 oligonucleotides are specific to the initial sequence and to clone C11, the L4 oligonucleotide is specific to the initial sequence and the U2 primer is specific to clone A3. A second 5'-RACE was carried out with oligonucleotides L3 and L7 located in the common region of the different clones (FIG. 2). The results obtained appear in FIGS. 3 and 4. The presence of different transcripts was confirmed by RT-PCR and nested RT-PCR (Table 2).

TABLE 2

| RT-PCR | Result | Secondary PCR C-B | Secondary PCR U3-B | Secondary PCR U5-L7 |
|---|---|---|---|---|
| U4-F | Smear | + | + | + |
| U5-F | Smear | + | + | + |
| U3-F | 1550 bp | + | + | |
| Expected Size (bp) | | 120 | 385 | 530 |

The primer and oligonucleotide sequence is provided in Tables 3 and 4 (SEQ ID NO: 16-37).

TABLE 3

| | | | SEQ ID |
|---|---|---|---|
| LY111_U4 | CCAGTTCTGCCTGTTCATC | 23 to 41 | 16 |
| LY111_U5 | TTCAAAACACAGAGGAGGAG | 319 to 338 | 17 |
| LY111_U3 | GAATTTGGTCAGTTTAGAGG | 759 to 778 | 18 |
| LY111_L7 | TTCTGGGATTTGGAGAGCTTTTTCAC | 851 to 825 | 19 |
| LY111_L6 | TCTGTCTGTCCCACACACTGCC | 914 to 892 | 20 |
| LY111_L3 | GACTGGCTCCGTCTCTCTG | 928 to 910 | 21 |
| LY111_C | AAGCAACAGAATCTCCCATCC | 1029 to 1049 | 22 |
| LY111_B | GCATTGTCAAAATTGCCCATC | 1147 To 1127 | 23 |
| LY111_E | AGGCGGAGAAATACGAAGAC | 1543 to 1562 | 24 |
| LY111_D | GCAGAGTGAGACAGCCCTTAAC | 1767 to 1746 | 25 |
| LY111_L2 | CTTCCTCAGGACTGGCGACTTCAG | 1811 to 1782 | 26 |
| LY111_L1 | CAAGCGGTCGTTCATTCCAAAGAG | 1934 to 1913 | 27 |
| LY111_F | AAGAGGAGATAACCCACCAGAG | 2288 to 2269 | 28 |

TABLE 4

| LY111_A | TCGTAGAGCAGCAGGTCCAAG | 14 to 34 | 46 |
|---|---|---|---|
| LY111_U1 | AGGGCTGCTGGCTATTTTC | 36 to 55 | 29 |
| LY111_L4 | TAAGAAATGGGTTGTGAAC | 148 to 166 | 30 |

TABLE 4-continued

| LY111_C | AAGCAACAGAATCTCCCATCC | 1029 to 1049 | 31 |
| --- | --- | --- | --- |
| LY111_B | GCATTGTCAAAATTGCCCATC | 1147 to 1127 | 32 |
| LY111_E | AGGCGGAGAAATACGAAGAC | 1543 to 1562 | 33 |
| LY111_D | GCAGAGTGAGACAGCCCTTAAC | 1767 to 1746 | 34 |
| LY111_L2 | CTTCCTCAGGACTGGCGACTTCAG | 1811 to 1782 | 35 |
| LY111_L1 | CAAGCGGTCGTTCATTCCAAAGAG | 1934 to 1913 | 36 |
| LY111_F | AAGAGGAGATAACCCACCAGAG | 2288 to 2269 | 37 |

All of these results make it possible to validate the consensus sequence which corresponds to the long isoform (FIG. 9, SEQ ID NO: 12 and 13) and the short isoform (FIG. 10, SEQ ID NO: 14 and 15) of the PAP1 protein which was identified from human lung. This protein is also referred to in the following examples as Ly111. The long isoform is encoded by an ORF of 1833 bp, located at residues 237-2069 of SEQ ID NO: 12 and comprises 610 amino acids. The polyadenylation signal is located from nucleotide 2315. The short isoform is encoded by an ORF of 942 bp, located at residues 429-1370 of SEQ ID NO: 14, and comprises 313 amino acids. The polyadenylation signal is located from nucleotide 1616.

Northern blot experiments were then performed on various human tissues with probes (amplimer CD and E-F) and made it possible to reveal a 6 kb transcript in the muscle, a transcript in the heart (3 kb), as well as a 6 kb transcript in the fetal liver. In addition, Example 7 describes the cloning of a transcript in the human fetal brain.

Various homology studies were carried out in different protein databases and the results thereof are presented in Table 5, below.

TABLE 5

| Library | Homology |
| --- | --- |
| Genpept116 | G5926736 (AB025258) granuphilin-a<br>Identity: 31% (215/679), Homology (POS): 46% (322/679)<br>G5926738 (AB025259) granuphilin-b<br>Identity: 31% (150/479), Homology (POS): 47% (230/479)<br>G1235722 (D70830) Doc2 beta (*homo sapiens*)<br>Identity: 25% (74/292), Homology (POS): 43% (127/292)<br>G289718 (L15302) Synaptogamin-I<br>Identity: 26% (77/293), Homology (POS): 45% (133/293) |
| Swissprot | SP: SYTI_CAEEL Synaptogamin I<br>Identity: 26% (77/293), Homology (POS): 45% (133/293)<br>SP: SYT2_MOUSE Synaptogamin II<br>Identity: 24% (72/293), Homology (POS): 44% (131/293) |

Example 7

Cloning of Two Full-Length PAP1 (LY111B) Transcripts from Complementary Human Fetal Brain DNA In order to confirm the presence of a full-length Ly111b transcript in the human brain, a PCR was performed from complementary DNA taken from human fetal brain (Marathon Ready cDNA, Clontech), by using the oligonucleotides LyF1 (AAT GGA AGG GCG TGA CGC, FIG. 5, SEQ ID NO: 38) and HA71 (CCT CAC GCC TGC TGC AAC CTG, SEQ ID NO: 39) as primers. A DNA fragment with low representation of approximately two kilobases was amplified. The product of this first PCR served as a matrix for a nested PCR, carried out with oligonucleotides LyEcoF (GCAC-GAATTC ATG GCC CAA GAA ATA GAT CTG, SEQ ID NO: 40) and HA72 (CTG TCT TCG TAT TTC TCC GCC TTG, SEQ ID NO: 41). The amplified products were digested with the restriction enzymes EcoRI (integrated into the oligonucleotide LyEcoF) and BstEII (FIG. 5) and inserted into the expression vector pcDNA3, then their sequence was determined. Analysis of the clone sequences obtained revealed the presence of two potential full-length Ly111b transcripts in the human fetal brain (FIG. 5). The first of these transcripts (Ly111b$_{fullA}$) corresponds to the mRNA which was identified in the human lung (Example 6) and encodes a protein of 609 amino acids (pLy111b$_{fullA}$; FIGS. 5, 6). The second (Ly111b$_{fullB}$) probably represents an alternative splicing product of a common primary mRNA. In this transcript, which is identical to Ly111b$_{fullA}$, the sequence between nucleotides 752 and 956 of the sequence validated in the human lung is absent. Ly111b$_{fullB}$ thus encodes a protein of 541 amino acids (pLy111b$_{fullB}$)(SEQ ID NO: 50) which is identical to pLy111$_{fullA}$ (SEQ ID NO: 48), in which, however, the domain included between amino acids 172 and 240 (FIGS. 5, 7) is missing. The two proteins pLy111b$_{fullA/fullB}$ integrate into the domain of interaction with the fragment of parkin that comprises amino acids 135 to 290, which were identified in the yeast (initial sequence Ly111b FIG. 5), and can therefore theoretically maintain this interaction.

The ply111b$_{fullA/fullB}$ Proteins Belong to the Rim/Rabphiline Family pLy111b$_{fullA/fullB}$ shows a homology with the proteins of the RIM/Rabphiline family (Wang Y. Sugita S & Sudhof T G. The RIM/NIM Family of Neuronal C2 Domain Proteins. *J. Biol Chem* (2000) 275.20033-20044) and in particular with the granulophilins (Wang Jie, Takeuchi T, Yokota H & Izumi T. Novel Rabphilin-3-like Protein Associates with Insulin-containing Granules in Pancreatic Beta Calls. *J. Biol Chem* (1999) 274, 28542-28548). They are characterized by the presence of a zinc finger domain in the N-terminal part of the two $C_2$ domains, in the C terminal part (FIGS. 6 and 7). The zinc finger domain of the proteins from the RIM/Rabphiline family was involved in the interaction with the Rab proteins. These Rab proteins, which bind GTP, are compounds which are essential to the machinery of membrane traffic in the eukaryotic cells. Moreover, it has been described that the $C_2$ domains of the proteins from the RIM/Rabphiline family can bind membranes by interacting with phospholipids.

Expression of the ply111b$_{fullA/fullB}$ Proteins in the Cells of the Cos-7 Line: Co-Localization with Parkin The coding sequence of the Ly111b$_{fullA,B}$ transcripts was inserted into the eukaryotic expression vector pcDNA3 in phase with the sequence which encodes a myc N-terminal epitope (pcDNA3-mycLy111b$_{fullA/B}$). Cells from the cos-7 line which are transfected using these vectors produce proteins with an apparent molecular weight of approximately 67 kDa (pcDNA3-mycLy111b$_{fullA}$) and 60 kDa (pcDNA3-mycLy111b$_{fullB}$), which corresponds to the expected molecular weight. These proteins, which were detected via immunolabelling, using an antibody directed against the N-terminal myc epitope, are distributed in the cytoplasm, the extensions and at times the nucleus of the cos-7 line of cells in a non-homogenous, punctate manner (FIG. 8a, b, column A). When these proteins are overexpressed with parkin and revealed using the Asp5 anti-parkin antibody in the cells of line cos-7

(FIG. 8a, b, column B) a similar distribution pattern and a co-localization of these proteins can be observed (FIG. 8a, b, column C).

BIBLIOGRAPHIC REFERENCES

Abbas, N. et al. (1999). A wide variety of mutations in the parkin gene are responsible for autosomal recessive parkinsonism in Europe. *Hum Mol Genet.* 8, 567-574.
Bartel, P. L. et al. (1993). D. A. Hartley Ed, Oxford University Press, 153
Chung, C. T. et al. (1989). One-step preparation of competent *Escherichia coli*: transformation and storage of bacterial cells in the same solution, *Proc. Natl. Acad Sci. USA.* 86, 2172-2175.
Fields, S. and Song, O. (1989). A novel genetic system to detect protein-protein interactions. *Nature.* 340, 245-246.
Gietz, R. D. et al. (1992). Improved method for high efficiency transformation of intact yeast cells. *Nucleic Acids Res.,* 20, 1425.
Hattori, N. et al. (1998). Molecular genetic analysis of a novel Parkin gene in Japanese families with autosomal recessive juvenile parkinsonism: evidence for variable homozygous deletions in the Parkin gene in affected individuals. *Ann Neurol.* 6, 935-941.
Kahn, A. et al., (1991) Thérapie génique: espoirs et limites, *Médecine et Sciences.* 7, 705-714.
Kitada, T. et al. (1998). Mutations in the parkin gene cause autosomal recessive juvenile parkinsonism. *Nature.* 392, 605-608.
Leroy, E. et al. (1998). The ubiquitin pathway in Parkinson's disease. *Nature.* 395, 451-452.
Lewy, F. H. (1912). in *Handbuch der Neurologie* (Lewandowski, M., ed) pp 920-933, Springer, Berlin.
Lucking, C. et al. (1998). Homozygous deletions in parkin gene in European and North African families with autosomal recessive juvenile parkinsonism. *Lancet.* 352, 1355-1356.
Maniatis, T. et al. (1989). Molecular cloning, second edition. Cold Spring Harbor Laboratory, Cold Spring Harbor, N.Y.
Morett, E. (1999). A novel transactivation domain in parkin. *Trends Biochem Sci.* 24, 229-231.
Peytavi, R. et al. (1999). HEED, the product of the human homolog of the murine eed gene, binds to the matrix protein of HIV-1. *J Biol. Chem.* 274, 1635-1645.
Polymeropoulos, M. H. et al. (1997). Mutation in the alpha-synuclein gene identified in families with Parkinson's disease. *Science.* 276, 2045-2047.
Sanger, F. et al. (1997). DNA sequencing with chain terminating inhibitors. *Proc. Natl. Acad. Sci. USA.* 74, 5463-5467.
Shimura, H. et al. (1999). Immunohistochemical and subcellular localization of Parkin protein: absence of protein in autosomal recessive juvenile parkinsonism patients. *Ann Neurol.* 45, 668-672.
Sunada, Y. et al. (1998), Differential expression of the parkin gene in the human brain and peripheral leukocytes. *Neurosci Lett.* 254, 180-182.
Vojtek, A B. et al., (1993). Mammalian Ras interacts directly with the serine/threonine kinase Raf. *Cell.* 74, 205-214.

The invention claimed is:

1. An isolated nucleic acid encoding a full length human PAP1 polypeptide compound having the sequence of SEQ ID NO:2.

2. An isolated nucleic acid according to claim 1, having the sequence of SEQ ID NO: 1.

3. A vector comprising a nucleic acid according to claim 1 or 2.

4. A recombinant-defective virus vector comprising a nucleic acid according to one of claim 1 or 2.

5. A method for producing a polypeptide compound comprising culturing a cell which contains the vector according to claim 3, under conditions for producing the human PAP1 polypeptide, and recovering the polypeptide compound produced.

6. An isolated host cell which contains the vector according to claim 3.

7. An isolated host cell which contains the vector according to claim 4.

* * * * *

SEQUENCE LISTING

```
<160> NUMBER OF SEQ ID NOS: 50

<210> SEQ ID NO 1
<211> LENGTH: 1313
<212> TYPE: DNA
<213> ORGANISM: Homo sapiens

<400> SEQUENCE: 1 cag aat ctc cca tcc agt ccg gca ccc agt acc ata ttc tct gga ggt        48
Gln Asn Leu Pro Ser Ser Pro Ala Pro Ser Thr Ile Phe Ser Gly Gly
  1               5                  10                  15 ttt aga cac gga agt tta att agc att gac agc acc tgt aca gag atg        96
Phe Arg His Gly Ser Leu Ile Ser Ile Asp Ser Thr Cys Thr Glu Met
             20                  25                  30 ggc aat ttt gac aat gct aat gtc act gga gaa ata gaa ttt gcc att       144
Gly Asn Phe Asp Asn Ala Asn Val Thr Gly Glu Ile Glu Phe Ala Ile
         35                  40                  45 cat tat tgc ttc aaa acc cat tct tta gaa ata tgc atc aag gcc tgt       192
His Tyr Cys Phe Lys Thr His Ser Leu Glu Ile Cys Ile Lys Ala Cys
     50                  55                  60 aag aac ctt gcc tat gga gaa gaa aag aag aaa aag tgc aat ccg tat       240
Lys Asn Leu Ala Tyr Gly Glu Glu Lys Lys Lys Lys Cys Asn Pro Tyr
 65                  70                  75                  80 gtg aag acc tac ctg ttg ccc gac aga tcc tcc cag gga aag cgc aag       288
Val Lys Thr Tyr Leu Leu Pro Asp Arg Ser Ser Gln Gly Lys Arg Lys
                 85                  90                  95 act gga gtc caa agg aac acc gtg gac ccg acc ttt cag gag acc ttg       336
Thr Gly Val Gln Arg Asn Thr Val Asp Pro Thr Phe Gln Glu Thr Leu
            100                 105                 110 aag tat cag gtg gcc cct gcc cag ctg gtg acc cgg cag ctg cag gtc       384
Lys Tyr Gln Val Ala Pro Ala Gln Leu Val Thr Arg Gln Leu Gln Val
```

```
                  115                 120                 125
tcg gtg tgg cat ctg ggc acg ctg gcc cgg aga gtg ttt ctt gga gaa      432
Ser Val Trp His Leu Gly Thr Leu Ala Arg Arg Val Phe Leu Gly Glu
    130                 135                 140 gtg atc att tct ctg gcc acg tgg gac ttt gaa gac agc aca aca cag      480
Val Ile Ile Ser Leu Ala Thr Trp Asp Phe Glu Asp Ser Thr Thr Gln
145                 150                 155                 160 tcc ttc cgc tgg cat ccg ctc cgg gcc aag gcg gag aaa tac gaa gac      528
Ser Phe Arg Trp His Pro Leu Arg Ala Lys Ala Glu Lys Tyr Glu Asp
                165                 170                 175 agc gtt cct cag agt aat gga gag ctc aca gtc cgg gct aag ctg gtt      576
Ser Val Pro Gln Ser Asn Gly Glu Leu Thr Val Arg Ala Lys Leu Val
            180                 185                 190 ctc cct tca cgg ccc aga aaa ctc caa gag gct caa gaa ggg aca gat      624
Leu Pro Ser Arg Pro Arg Lys Leu Gln Glu Ala Gln Glu Gly Thr Asp
        195                 200                 205 cag cca tca ctt cat ggt caa ctt tgt ttg gta gtg cta gga gcc aag      672
Gln Pro Ser Leu His Gly Gln Leu Cys Leu Val Val Leu Gly Ala Lys
    210                 215                 220 aat tta cct gtg cgg cca gat ggc acc ttg aac tca ttt gtt aag ggc      720
Asn Leu Pro Val Arg Pro Asp Gly Thr Leu Asn Ser Phe Val Lys Gly
225                 230                 235                 240 tgt ctc act ctg cca gac caa caa aaa ctg aga ctg aag tcg cca gtc      768
Cys Leu Thr Leu Pro Asp Gln Gln Lys Leu Arg Leu Lys Ser Pro Val
                245                 250                 255 ctg agg aag cag gct tgc ccc cag tgg aaa cac tca ttt gtc ttc agt      816
Leu Arg Lys Gln Ala Cys Pro Gln Trp Lys His Ser Phe Val Phe Ser
            260                 265                 270 ggc gta acc cca gct cag ctg agg cag tcg agc ttg gag tta act gtc      864
Gly Val Thr Pro Ala Gln Leu Arg Gln Ser Ser Leu Glu Leu Thr Val
        275                 280                 285 tgg gat cag gcc ctc ttt gga atg aat gac cgc ttg ctt gga gga acc      912
Trp Asp Gln Ala Leu Phe Gly Met Asn Asp Arg Leu Leu Gly Gly Thr
    290                 295                 300 aga ctt ggt tca aag gga gac aca gct gtt ggc ggg gat gca tgc tca      960
Arg Leu Gly Ser Lys Gly Asp Thr Ala Val Gly Gly Asp Ala Cys Ser
305                 310                 315                 320 cta tcg aag ctc cag tgg cag aaa gtc ctt tcc agc ccc aat cta tgg     1008
Leu Ser Lys Leu Gln Trp Gln Lys Val Leu Ser Ser Pro Asn Leu Trp
                325                 330                 335 aca gac atg act ctt gtc ctg cac tgacatgaag gcctcaaggt tccaggttgc    1062
Thr Asp Met Thr Leu Val Leu His
            340 agcaggcgtg aggcactgtg cgtctgcaga ggggctacga accaggtgca gggtcccagc   1122 tggagacccc tttgaccttg agcagtctcc atctgcggcc ctgtcccatg cttaaccgc    1182 ctattggtat ctgtgtatat ttacgttaaa cacaattatg ttacctaagc ctctggtggg   1242 ttatctcctc tttgagatgt agaaaatggc cagattttaa taaacgttgt tacccatgaa   1302 aaaaaaaaaa a                                                       1313

<210> SEQ ID NO 2
<211> LENGTH: 344
<212> TYPE: PRT
<213> ORGANISM: Homo sapiens

<400> SEQUENCE: 2

Gln Asn Leu Pro Ser Ser Pro Ala Pro Ser Thr Ile Phe Ser Gly Gly
1               5                   10                  15

Phe Arg His Gly Ser Leu Ile Ser Ile Asp Ser Thr Cys Thr Glu Met
```

```
                    20                  25                  30
Gly Asn Phe Asp Asn Ala Asn Val Thr Gly Glu Ile Glu Phe Ala Ile
            35                  40                  45

His Tyr Cys Phe Lys Thr His Ser Leu Glu Ile Cys Ile Lys Ala Cys
 50                  55                  60

Lys Asn Leu Ala Tyr Gly Glu Glu Lys Lys Lys Cys Asn Pro Tyr
 65                  70                  75                  80

Val Lys Thr Tyr Leu Leu Pro Asp Arg Ser Ser Gln Gly Lys Arg Lys
                    85                  90                  95

Thr Gly Val Gln Arg Asn Thr Val Asp Pro Thr Phe Gln Glu Thr Leu
                100                 105                 110

Lys Tyr Gln Val Ala Pro Ala Gln Leu Val Thr Arg Gln Leu Gln Val
            115                 120                 125

Ser Val Trp His Leu Gly Thr Leu Ala Arg Arg Val Phe Leu Gly Glu
130                 135                 140

Val Ile Ile Ser Leu Ala Thr Trp Asp Phe Glu Asp Ser Thr Thr Gln
145                 150                 155                 160

Ser Phe Arg Trp His Pro Leu Arg Ala Lys Ala Glu Lys Tyr Glu Asp
                165                 170                 175

Ser Val Pro Gln Ser Asn Gly Glu Leu Thr Val Arg Ala Lys Leu Val
            180                 185                 190

Leu Pro Ser Arg Pro Arg Lys Leu Gln Glu Ala Gln Glu Gly Thr Asp
                195                 200                 205

Gln Pro Ser Leu His Gly Gln Leu Cys Leu Val Val Leu Gly Ala Lys
        210                 215                 220

Asn Leu Pro Val Arg Pro Asp Gly Thr Leu Asn Ser Phe Val Lys Gly
225                 230                 235                 240

Cys Leu Thr Leu Pro Asp Gln Gln Lys Leu Arg Leu Lys Ser Pro Val
                245                 250                 255

Leu Arg Lys Gln Ala Cys Pro Trp Lys His Ser Phe Val Phe Ser
                260                 265                 270

Gly Val Thr Pro Ala Gln Leu Arg Gln Ser Ser Leu Glu Leu Thr Val
            275                 280                 285

Trp Asp Gln Ala Leu Phe Gly Met Asn Asp Arg Leu Leu Gly Gly Thr
290                 295                 300

Arg Leu Gly Ser Lys Gly Asp Thr Ala Val Gly Gly Asp Ala Cys Ser
305                 310                 315                 320

Leu Ser Lys Leu Gln Trp Gln Lys Val Leu Ser Ser Pro Asn Leu Trp
                325                 330                 335

Thr Asp Met Thr Leu Val Leu His
            340

<210> SEQ ID NO 3
<211> LENGTH: 471
<212> TYPE: DNA
<213> ORGANISM: Homo sapiens
<220> FEATURE:
<221> NAME/KEY: CDS
<222> LOCATION: (1)..(471)

<400> SEQUENCE: 3 gga agt cca gca ggt aga tca atc tac aac agc ttt tat gtg tat tgc     48
Gly Ser Pro Ala Gly Arg Ser Ile Tyr Asn Ser Phe Tyr Val Tyr Cys
 1               5                  10                  15 aaa ggc ccc tgt caa aga gtg cag ccg gga aaa ctc agg gta cag tgc     96
Lys Gly Pro Cys Gln Arg Val Gln Pro Gly Lys Leu Arg Val Gln Cys
            20                  25                  30
```

```
agc acc tgc agg cag gca acg ctc acc ttg acc cag ggt cca tct tgc      144
Ser Thr Cys Arg Gln Ala Thr Leu Thr Leu Thr Gln Gly Pro Ser Cys
     35                  40                  45 tgg gat gat gtt tta att cca aac cgg atg agt ggt gaa tgc caa tcc      192
Trp Asp Asp Val Leu Ile Pro Asn Arg Met Ser Gly Glu Cys Gln Ser
 50                  55                  60 cca cac tgc cct ggg act agt gca gaa ttt ttc ttt aaa tgt gga gca      240
Pro His Cys Pro Gly Thr Ser Ala Glu Phe Phe Phe Lys Cys Gly Ala
 65                  70                  75                  80 cac ccc acc tct gac aag gaa aca tca gta gct ttg cac ctg atc gca      288
His Pro Thr Ser Asp Lys Glu Thr Ser Val Ala Leu His Leu Ile Ala
                 85                  90                  95 aca aat agt cgg aac atc act tgc att acg tgc aca gac gtc agg agc      336
Thr Asn Ser Arg Asn Ile Thr Cys Ile Thr Cys Thr Asp Val Arg Ser
                100                 105                 110 ccc gtc ctg gtt ttc cag tgc aac tcc cgc cac gtg att tgc tta gac      384
Pro Val Leu Val Phe Gln Cys Asn Ser Arg His Val Ile Cys Leu Asp
            115                 120                 125 tgt ttc cac tta tac tgt gtg aca aga ctc aat gat cgg cag ttt gtt      432
Cys Phe His Leu Tyr Cys Val Thr Arg Leu Asn Asp Arg Gln Phe Val
    130                 135                 140 cac gac cct caa ctt ggc tac tcc ctg cct tgt gtg tag                  471
His Asp Pro Gln Leu Gly Tyr Ser Leu Pro Cys Val
145                 150                 155
```

<210> SEQ ID NO 4
<211> LENGTH: 156
<212> TYPE: PRT
<213> ORGANISM: Homo sapiens

<400> SEQUENCE: 4

```
Gly Ser Pro Ala Gly Arg Ser Ile Tyr Asn Ser Phe Tyr Val Tyr Cys
 1               5                  10                  15

Lys Gly Pro Cys Gln Arg Val Gln Pro Gly Lys Leu Arg Val Gln Cys
             20                  25                  30

Ser Thr Cys Arg Gln Ala Thr Leu Thr Leu Thr Gln Gly Pro Ser Cys
         35                  40                  45

Trp Asp Asp Val Leu Ile Pro Asn Arg Met Ser Gly Glu Cys Gln Ser
 50                  55                  60

Pro His Cys Pro Gly Thr Ser Ala Glu Phe Phe Phe Lys Cys Gly Ala
 65                  70                  75                  80

His Pro Thr Ser Asp Lys Glu Thr Ser Val Ala Leu His Leu Ile Ala
                 85                  90                  95

Thr Asn Ser Arg Asn Ile Thr Cys Ile Thr Cys Thr Asp Val Arg Ser
                100                 105                 110

Pro Val Leu Val Phe Gln Cys Asn Ser Arg His Val Ile Cys Leu Asp
            115                 120                 125

Cys Phe His Leu Tyr Cys Val Thr Arg Leu Asn Asp Arg Gln Phe Val
    130                 135                 140

His Asp Pro Gln Leu Gly Tyr Ser Leu Pro Cys Val
145                 150                 155
```

<210> SEQ ID NO 5
<211> LENGTH: 27
<212> TYPE: DNA
<213> ORGANISM: Artificial sequence
<220> FEATURE:
<223> OTHER INFORMATION: Description of the artificial sequence: Oligonucleotide

```
<400> SEQUENCE: 5
ttaagaattc ggaagtccag caggtag                                       27

<210> SEQ ID NO 6
<211> LENGTH: 29
<212> TYPE: DNA
<213> ORGANISM: Artificial sequence
<220> FEATURE:
<223> OTHER INFORMATION: Description of the artificial sequence:
      Oligonucleotide

<400> SEQUENCE: 6
attaggatcc ctacacacaa ggcagggag                                     29

<210> SEQ ID NO 7
<211> LENGTH: 19
<212> TYPE: DNA
<213> ORGANISM: Artificial sequence
<220> FEATURE:
<223> OTHER INFORMATION: Description of the artificial sequence:
      Oligonucleotide

<400> SEQUENCE: 7
gcgtttggaa tcactacag                                                19

<210> SEQ ID NO 8
<211> LENGTH: 17
<212> TYPE: DNA
<213> ORGANISM: Artificial sequence
<220> FEATURE:
<223> OTHER INFORMATION: Description of the artificial sequence:
      Oligonucleotide

<400> SEQUENCE: 8
ggtctcggtg tggcatc                                                  17

<210> SEQ ID NO 9
<211> LENGTH: 18
<212> TYPE: DNA
<213> ORGANISM: Artificial sequence
<220> FEATURE:
<223> OTHER INFORMATION: Description of the artificial sequence:
      Oligonucleotide

<400> SEQUENCE: 9
ccgcttgctt ggaggaac                                                 18

<210> SEQ ID NO 10
<211> LENGTH: 18
<212> TYPE: DNA
<213> ORGANISM: Artificial sequence
<220> FEATURE:
<223> OTHER INFORMATION: Description of the artificial sequence:
      Oligonucleotide

<400> SEQUENCE: 10
cgtatttctc cgccttgg                                                 18

<210> SEQ ID NO 11
<211> LENGTH: 28
<212> TYPE: DNA
<213> ORGANISM: Artificial sequence
<220> FEATURE:
<223> OTHER INFORMATION: Description of the artificial sequence:
      Oligonucleotide

<400> SEQUENCE: 11
```
aatagctcga gtcagtgcag gacaagag                                          28

<210> SEQ ID NO 12
<211> LENGTH: 2347
<212> TYPE: DNA
<213> ORGANISM: Homo sapiens

<400> SEQUENCE: 12

| | | | | | |
|---|---|---|---|---|---|
| ggccttgggg | cactgaggga | tgccagttct | gcctgttcat | ctggaacctg | gatctaagga | 60 |
| gggaagaggc | gttgcccctg | ctggcatagt | caggtaccag | cccagccagg | tattgaacgg | 120 |
| gctgagcttt | tcatgatggt | tcctgctgac | ctggaaacat | cttaaatgga | agggcgtgag | 180 |
| cgcttggtcc | atgcagtgaa | gctcttccaa | cctgggtcaa | cgaaaacgga | gaagaaatgg | 240 |
| cccaagaaat | agatctgagt | gctctcaagg | agttagaacg | cgaggccatt | ctccaggtcc | 300 |
| tgtaccgaga | ccaggcggtt | caaaacacag | aggaggagag | gacacggaaa | ctgaaaacac | 360 |
| acctgcagca | tctccggtgg | aaaggagcga | agaacacgga | ctgggagcac | aaagagaagt | 420 |
| gctgtgcgcg | ctgccagcag | gtgctggggt | tcctgctgca | ccggggcgcc | gtgtgccggg | 480 |
| gctgcagcca | ccgcgtgtgt | gcccagtgcc | gagtgttcct | gaggggggacc | catgcctgga | 540 |
| agtgcacggt | gtgcttcgag | gacaggaatg | tcaaaataaa | aactggagaa | tggttctatg | 600 |
| aggaacgagc | caagaaattt | ccaactggag | gcaaacatga | gacagttgga | gggcagctct | 660 |
| tgcaatctta | tcagaagctg | agcaaaattt | ctgtggttcc | tcctactcca | cctcctgtca | 720 |
| gcgagagcca | gtgcagccgc | agtcctggca | ggttacagga | atttggtcag | tttagaggat | 780 |
| ttaataagtc | cgtggaaaat | ttgttttctgt | ctcttgctac | ccacgtgaaa | aagctctcca | 840 |
| aatcccagaa | tgatatgact | tctgagaagc | atcttctcgc | cacgggcccc | aggcagtgtg | 900 |
| tgggacagac | agagagacgg | agccagtctg | acactgcggt | caacgtcacc | accaggaagg | 960 |
| tcagtgcacc | agatattctg | aaacctctca | atcaagagga | tcccaaatgc | tctactaacc | 1020 |
| ctattttgaa | gcaacagaat | ctcccatcca | gtccggcacc | cagtaccata | ttctctggag | 1080 |
| gttttagaca | cggaagttta | attagcattg | acagcacctg | tacagagatg | gcaattttttg | 1140 |
| acaatgctaa | tgtcactgga | gaaatagaat | ttgccattca | ttattgcttc | aaaacccatt | 1200 |
| ctttagaaat | atgcatcaag | gcctgtaaga | accttgccta | tggagaagaa | aagaagaaaa | 1260 |
| agtgcaatcc | gtatgtgaag | acctacctgt | tgcccgacag | atcctcccag | ggaaagcgca | 1320 |
| agactggagt | ccaaaggaac | accgtggacc | cgaccttttca | ggagaccttg | aagtatcagg | 1380 |
| tggcccctgc | ccagctggtg | acccggcagc | tgcaggtctc | ggtgtggcat | ctgggcacgc | 1440 |
| tggcccggag | agtgtttctt | ggagaagtga | tcattcctct | ggccacgtgg | gactttgaag | 1500 |
| acagcacaac | acagtccttc | cgctggcatc | cgctccgggc | caaggcggag | aaatacgaag | 1560 |
| acagcgttcc | tcagagtaat | ggagagctca | cagtccgggc | taagctggtt | ctcccttcac | 1620 |
| ggcccagaaa | actccaagag | gctcaagaag | ggacagatca | gccatcactt | catggtcaac | 1680 |
| tttgtttggt | agtgctagga | gccaagaatt | tacctgtgcg | gccagatggc | accttgaact | 1740 |
| catttgttaa | gggctgtctc | actctgccag | accaacaaaa | actgagactg | aagtcgccag | 1800 |
| tcctgaggaa | gcaggcttgc | ccccagtgga | acactcatt | tgtcttcagt | ggcgtaaccc | 1860 |
| cagctcagct | gaggcagtcg | agcttggagt | taactgtctg | ggatcaggcc | ctcttttggaa | 1920 |
| tgaacgaccg | cttgcttgga | ggaaccagac | ttggttcaaa | gggagacaca | gctgttggcg | 1980 |
| gggatgcatg | ctcacaatcg | aagctccagt | ggcagaaagt | cctttccagc | cccaatctat | 2040 |
| ggacagacat | gactcttgtc | ctgcactgac | atgaaggcct | caaggttcca | ggttgcagca | 2100 |

-continued

```
ggcgtgaggc actgtgcgtc tgcagagggg ctacgaacca ggtgcagggt cccagctgga    2160
gacccctttg accttgagca gtctccatct gcggccctgt cccatggctt aaccgcctat    2220
tggtatctgt gtatatttac gttaaacaca attatgttac ctaagcctct ggtgggttat    2280
ctcctctttg agatgtagaa aatggccaga ttttaataaa cgttgttacc catgaaaaaa    2340
aaaaaaa                                                              2347
```

<210> SEQ ID NO 13
<211> LENGTH: 610
<212> TYPE: PRT
<213> ORGANISM: Homo sapiens

<400> SEQUENCE: 13

```
Met Ala Gln Glu Ile Asp Leu Ser Ala Leu Lys Glu Leu Arg Glu
 1               5                  10                  15

Ala Ile Leu Gln Val Leu Tyr Arg Asp Gln Ala Val Gln Asn Thr Glu
                20                  25                  30

Glu Glu Arg Thr Arg Lys Leu Lys Thr His Leu Gln His Leu Arg Trp
            35                  40                  45

Lys Gly Ala Lys Asn Thr Asp Trp Glu His Lys Glu Lys Cys Cys Ala
        50                  55                  60

Arg Cys Gln Gln Val Leu Gly Phe Leu Leu His Arg Gly Ala Val Cys
    65                  70                  75                  80

Arg Gly Cys Ser His Arg Val Cys Ala Gln Cys Arg Val Phe Leu Arg
                85                  90                  95

Gly Thr His Ala Trp Lys Cys Thr Val Cys Phe Glu Asp Arg Asn Val
                100                 105                 110

Lys Ile Lys Thr Gly Glu Trp Phe Tyr Glu Glu Arg Ala Lys Lys Phe
            115                 120                 125

Pro Thr Gly Gly Lys His Glu Thr Val Gly Gly Gln Leu Leu Gln Ser
        130                 135                 140

Tyr Gln Lys Leu Ser Lys Ile Ser Val Val Pro Thr Pro Pro
145                 150                 155                 160

Val Ser Glu Ser Gln Cys Ser Arg Ser Pro Gly Arg Leu Gln Glu Phe
                165                 170                 175

Gly Gln Phe Arg Gly Phe Asn Lys Ser Val Glu Asn Leu Phe Leu Ser
            180                 185                 190

Leu Ala Thr His Val Lys Lys Leu Ser Lys Ser Gln Asn Asp Met Thr
        195                 200                 205

Ser Glu Lys His Leu Leu Ala Thr Gly Pro Arg Gln Cys Val Gly Gln
    210                 215                 220

Thr Glu Arg Arg Ser Gln Ser Asp Thr Ala Val Asn Val Thr Arg
225                 230                 235                 240

Lys Val Ser Ala Pro Asp Ile Leu Lys Pro Leu Asn Gln Glu Asp Pro
                245                 250                 255

Lys Cys Ser Thr Asn Pro Ile Leu Lys Gln Gln Asn Leu Pro Ser Ser
            260                 265                 270

Pro Ala Pro Ser Thr Ile Phe Ser Gly Gly Phe Arg His Gly Ser Leu
        275                 280                 285

Ile Ser Ile Asp Ser Thr Cys Thr Glu Met Gly Asn Phe Asp Asn Ala
    290                 295                 300

Asn Val Thr Gly Glu Ile Glu Phe Ala Ile His Tyr Cys Phe Lys Thr
305                 310                 315                 320

His Ser Leu Glu Ile Cys Ile Lys Ala Cys Lys Asn Leu Ala Tyr Gly
                325                 330                 335
```

```
Glu Glu Lys Lys Lys Lys Cys Asn Pro Tyr Val Lys Thr Tyr Leu Leu
            340                 345                 350
Pro Asp Arg Ser Ser Gln Gly Lys Arg Lys Thr Gly Val Gln Arg Asn
            355                 360                 365
Thr Val Asp Pro Thr Phe Gln Glu Thr Leu Lys Tyr Gln Val Ala Pro
            370                 375                 380
Ala Gln Leu Val Thr Arg Gln Leu Gln Val Ser Val Trp His Leu Gly
385                 390                 395                 400
Thr Leu Ala Arg Arg Val Phe Leu Gly Glu Val Ile Ile Pro Leu Ala
                405                 410                 415
Thr Trp Asp Phe Glu Asp Ser Thr Thr Gln Ser Phe Arg Trp His Pro
                420                 425                 430
Leu Arg Ala Lys Ala Glu Lys Tyr Glu Asp Ser Val Pro Gln Ser Asn
            435                 440                 445
Gly Glu Leu Thr Val Arg Ala Lys Leu Val Leu Pro Ser Arg Pro Arg
450                 455                 460
Lys Leu Gln Glu Ala Gln Glu Gly Thr Asp Gln Pro Ser Leu His Gly
465                 470                 475                 480
Gln Leu Cys Leu Val Leu Gly Ala Lys Asn Leu Pro Val Arg Pro
                485                 490                 495
Asp Gly Thr Leu Asn Ser Phe Val Lys Gly Cys Leu Thr Leu Pro Asp
                500                 505                 510
Gln Gln Lys Leu Arg Leu Lys Ser Pro Val Leu Arg Lys Gln Ala Cys
            515                 520                 525
Pro Gln Trp Lys His Ser Phe Val Phe Ser Gly Val Thr Pro Ala Gln
            530                 535                 540
Leu Arg Gln Ser Ser Leu Glu Leu Thr Val Trp Asp Gln Ala Leu Phe
545                 550                 555                 560
Gly Met Asn Asp Arg Leu Leu Gly Gly Thr Arg Leu Gly Ser Lys Gly
                565                 570                 575
Asp Thr Ala Val Gly Gly Asp Ala Cys Ser Gln Ser Lys Leu Gln Trp
                580                 585                 590
Gln Lys Val Leu Ser Ser Pro Asn Leu Trp Thr Asp Met Thr Leu Val
            595                 600                 605
Leu His
    610

<210> SEQ ID NO 14
<211> LENGTH: 1648
<212> TYPE: DNA
<213> ORGANISM: Homo sapiens

<400> SEQUENCE: 14
gaaatcatgc ccctcgtaga gcagcaggtc caagcagggc tgctggctat ttttccaaaa      60
agtgaggcag tttaaaaaaa aggcggagaa ctagaattat agaataatgg cacattttgt     120
gtatttgtaa aactaacggc ttgcatggtt cacaacccat ttcttatgcc tgtgttttcc     180
ttggcagcaa aatttctgtg gttcctccta ctccacctcc tgtcagcgag agccagtgca     240
gccgcagtcc tggcaggaag gtcagtgcac cagatattct gaaacctctc aatcaagagg     300
atcccaaatg ctctactaac cctatttga agcaacagaa tctcccatcc agtccggcac     360
ccagtaccat attctctgga ggttttagac acggaagttt aattagcatt gacagcacct     420
gtacagagat gggcaatttt gacaatgcta atgtcactgg agaaatagaa tttgccattc     480
attattgctt caaaacccat tctttagaaa tatgcatcaa ggcctgtaag aaccttgcct     540
```

-continued

```
atggagaaga aaagaagaaa aagtgcaatc cgtatgtgaa gacctacctg ttgcccgaca       600
gatcctccca gggaaagcgc aagactggag tccaaaggaa caccgtggac ccgaccttc       660
aggagacctt gaagtatcag gtggcccctg cccagctggt gacccggcag ctgcaggtct       720
cggtgtggca tctgggcacg ctggcccgga gagtgtttct tggagaagtg atcattcctc       780
tggccacgtg ggactttgaa gacagcacaa cacagtcctt ccgctggcat ccgctccggg       840
ccaaggcgga gaaatacgaa gacagcgttc ctcagagtaa tggagagctc acagtccggg       900
ctaagctggt tctcccttca cggcccagaa aactccaaga ggctcaagaa gggacagatc       960
agccatcact tcatggtcaa ctttgtttgg tagtgctagg agccaagaat ttacctgtgc      1020
ggccagatgg caccttgaac tcatttgtta agggctgtct cactctgcca gaccaacaaa      1080
aactgagact gaagtcgcca gtcctgagga agcaggcttg cccccagtgg aaacactcat      1140
ttgtcttcag tggcgtaacc ccagctcagc tgaggcagtc gagcttggag ttaactgtct      1200
gggatcaggc cctcttgga atgaacgacc gcttgcttgg aggaaccaga cttggttcaa      1260
agggagacac agctgttggc ggggatgcat gctcacaatc gaagctccag tggcagaaag      1320
tcctttccag ccccaatcta tggacagaca tgactcttgt cctgcactga catgaaggcc      1380
tcaaggttcc aggttgcagc aggcgtgagg cactgtgcgt ctgcagaggg gctacgaacc      1440
aggtgcaggg tccagctgg agacccttt gaccttgagc agtctccatc tgcggccctg      1500
tcccatggct taaccgccta ttggtatctg tgtatattta cgttaaacac aattatgtta      1560
cctaagcctc tggtgggtta tctcctcttt gagatgtaga aaatggccag attttaataa      1620
acgttgttac ccatgaaaaa aaaaaaaa                                        1648
```

<210> SEQ ID NO 15
<211> LENGTH: 313
<212> TYPE: PRT
<213> ORGANISM: Homo sapiens

<400> SEQUENCE: 15

```
Met Gly Asn Phe Asp Asn Ala Asn Val Thr Gly Glu Ile Glu Phe Ala
  1               5                  10                  15

Ile His Tyr Cys Phe Lys Thr His Ser Leu Glu Ile Cys Ile Lys Ala
             20                  25                  30

Cys Lys Asn Leu Ala Tyr Gly Glu Lys Lys Lys Cys Asn Pro
         35                  40                  45

Tyr Val Lys Thr Tyr Leu Leu Pro Asp Arg Ser Ser Gln Gly Lys Arg
     50                  55                  60

Lys Thr Gly Val Gln Arg Asn Thr Val Asp Pro Thr Phe Gln Glu Thr
 65                  70                  75                  80

Leu Lys Tyr Gln Val Ala Pro Ala Gln Leu Val Thr Arg Gln Leu Gln
                 85                  90                  95

Val Ser Val Trp His Leu Gly Thr Leu Ala Arg Arg Val Phe Leu Gly
            100                 105                 110

Glu Val Ile Ile Pro Leu Ala Thr Trp Asp Phe Glu Asp Ser Thr Thr
        115                 120                 125

Gln Ser Phe Arg Trp His Pro Leu Arg Ala Lys Ala Glu Lys Tyr Glu
    130                 135                 140

Asp Ser Val Pro Gln Ser Asn Gly Glu Leu Thr Val Arg Ala Lys Leu
145                 150                 155                 160

Val Leu Pro Ser Arg Pro Arg Lys Leu Gln Glu Ala Gln Glu Gly Thr
                165                 170                 175
```

```
Asp Gln Pro Ser Leu His Gly Gln Leu Cys Leu Val Val Leu Gly Ala
                180                 185                 190

Lys Asn Leu Pro Val Arg Pro Asp Gly Thr Leu Asn Ser Phe Val Lys
            195                 200                 205

Gly Cys Leu Thr Leu Pro Asp Gln Gln Lys Leu Arg Leu Lys Ser Pro
210                 215                 220

Val Leu Arg Lys Gln Ala Cys Pro Gln Trp Lys His Ser Phe Val Phe
225                 230                 235                 240

Ser Gly Val Thr Pro Ala Gln Leu Arg Gln Ser Ser Leu Glu Leu Thr
                245                 250                 255

Val Trp Asp Gln Ala Leu Phe Gly Met Asn Asp Arg Leu Leu Gly Gly
                260                 265                 270

Thr Arg Leu Gly Ser Lys Gly Asp Thr Ala Val Gly Gly Asp Ala Cys
            275                 280                 285

Ser Gln Ser Lys Leu Gln Trp Gln Lys Val Leu Ser Ser Pro Asn Leu
                290                 295                 300

Trp Thr Asp Met Thr Leu Val Leu His
305                 310
```

<210> SEQ ID NO 16
<211> LENGTH: 19
<212> TYPE: DNA
<213> ORGANISM: Artificial sequence
<220> FEATURE:
<223> OTHER INFORMATION: Description of the artificial sequence: oligonucleotide

<400> SEQUENCE: 16
ccagttctgc ctgttcatc                                            19

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence: oligonucleotide

<400> SEQUENCE: 17
ttcaaaacac agaggaggag                                           20

<210> SEQ ID NO 18
<211> LENGTH: 20
<212> TYPE: DNA
<213> ORGANISM: Artificial sequence
<220> FEATURE:
<223> OTHER INFORMATION: Description of the artificial sequence: oligonucleotide

<400> SEQUENCE: 18
gaatttggtc agtttagagg                                           20

<210> SEQ ID NO 19
<211> LENGTH: 26
<212> TYPE: DNA
<213> ORGANISM: Artificial sequence
<220> FEATURE:
<223> OTHER INFORMATION: Description of the artificial sequence: oligonucleotide

<400> SEQUENCE: 19
ttctgggatt tggagagctt tttcac                                    26

```
<210> SEQ ID NO 20
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 20
tctgtctgtc ccacacactg cc                                              22

<210> SEQ ID NO 21
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 21
gactggctcc gtctctctg                                                  19

<210> SEQ ID NO 22
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 22
aagcaacaga atctcccatc c                                               21

<210> SEQ ID NO 23
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 23
gcattgtcaa aattgcccat c                                               21

<210> SEQ ID NO 24
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 24
aggcggagaa atacgaagac                                                 20

<210> SEQ ID NO 25
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 25
gcagagtgag acagcccttg ac                                              22

<210> SEQ ID NO 26
<211> LENGTH: 24
```

```
<212> TYPE: DNA
<213> ORGANISM: Artificial sequence
<220> FEATURE:
<223> OTHER INFORMATION: Description of the artificial sequence:
      oligonucleotide

<400> SEQUENCE: 26
cttcctcagg actggcgact tcag                                           24

<210> SEQ ID NO 27
<211> LENGTH: 24
<212> TYPE: DNA
<213> ORGANISM: Artificial sequence
<220> FEATURE:
<223> OTHER INFORMATION: Description of the artificial sequence:
      oligonucleotide

<400> SEQUENCE: 27
caagcggtcg ttcattccaa agag                                           24

<210> SEQ ID NO 28
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 28
aagaggagat aacccaccag ag                                             22

<210> SEQ ID NO 29
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 29
agggctgctg gctattttc                                                 20

<210> SEQ ID NO 30
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 30
taagaaatgg gttgtgaac                                                 19

<210> SEQ ID NO 31
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 31
aagcaacaga atctcccatc c                                              21

<210> SEQ ID NO 32
<211> LENGTH: 21
<212> TYPE: DNA
<213> ORGANISM: Artificial sequence
```

-continued

<220> FEATURE:
<223> OTHER INFORMATION: Description of the artificial sequence:
      oligonucleotide

<400> SEQUENCE: 32
gcattgtcaa aattgcccat c                                         21

<210> SEQ ID NO 33
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 33
aggcggagaa atacgaagac                                           20

<210> SEQ ID NO 34
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 34
gcagagtgag acagcccetta ac                                       22

<210> SEQ ID NO 35
<211> LENGTH: 24
<212> TYPE: DNA
<213> ORGANISM: Artificial sequence
<220> FEATURE:
<223> OTHER INFORMATION: Description of the artificial sequence:
      oligonucleotide

<400> SEQUENCE: 35
cttcctcagg actggcgact tcag                                      24

<210> SEQ ID NO 36
<211> LENGTH: 24
<212> TYPE: DNA
<213> ORGANISM: Artificial sequence
<220> FEATURE:
<223> OTHER INFORMATION: Description of the artificial sequence:
      oligonucleotide

<400> SEQUENCE: 36
caagcggtcg ttcattccaa agag                                      24

<210> SEQ ID NO 37
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 37
aagaggagat aacccaccag ag                                        22

<210> SEQ ID NO 38
<211> LENGTH: 18
<212> TYPE: DNA
<213> ORGANISM: Artificial sequence
<220> FEATURE:
<223> OTHER INFORMATION: Description of the artificial sequence:

```
                            oligonucleotide

<400> SEQUENCE: 38
aatggaaggg cgtgacgc                                                   18

<210> SEQ ID NO 39
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 39
cctcacgcct gctgcaacct g                                               21

<210> SEQ ID NO 40
<211> LENGTH: 31
<212> TYPE: DNA
<213> ORGANISM: Artificial sequence
<220> FEATURE:
<223> OTHER INFORMATION: Description of the artificial sequence:
      oligonucleotide

<400> SEQUENCE: 40
gcacgaattc atggcccaag aaatagatct g                                    31

<210> SEQ ID NO 41
<211> LENGTH: 24
<212> TYPE: DNA
<213> ORGANISM: Artificial sequence
<220> FEATURE:
<223> OTHER INFORMATION: Description of the artificial sequence:
      oligonucleotide

<400> SEQUENCE: 41
ctgtcttcgt atttctccgc cttg                                            24

<210> SEQ ID NO 42
<211> LENGTH: 2347
<212> TYPE: DNA
<213> ORGANISM: Homo sapiens
<220> FEATURE:
<223> OTHER INFORMATION: Delete: this sequence is a duplicate of
      Sequence 12

<400> SEQUENCE: 42
ggccttgggg cactgaggga tgccagttct gcctgttcat ctggaacctg gatctaagga     60
gggaagaggc gttgcccctg ctggcatagt caggtaccag cccagccagg tattgaacgg    120
gctgagcttt tcatgatggt tcctgctgac ctggaaacat cttaaatgga agggcgtgag    180
cgcttggtcc atgcagtgaa gctcttccaa cctgggtcaa cgaaaacgga gaagaaatgg    240
cccaagaaat agatctgagt gctctcaagg agttagaacg cgaggccatt ctccaggtcc    300
tgtaccgaga ccaggcggtt caaaacacag aggaggagag gacacggaaa ctgaaaacac    360
acctgcagca tctccggtgg aaaggagcga agaacacgga ctgggagcac aaagagaagt    420
gctgtgcgcg ctgccagcag gtgctggggt tcctgctgca ccggggcgcc gtgtgccggg    480
gctgcagcca ccgcgtgtgt gcccagtgcc gagtgttcct gagggggacc catgcctgga    540
agtgcacggt gtgcttcgag gacaggaatg tcaaaataaa aactggagaa tggttctata    600
aggaacgagc caagaaattt ccaactggag gcaaacatga gacagttgga gggcagctct    660
tgcaatctta tcagaagctg agcaaaattt ctgtggttcc tcctactcca cctcctgtca    720
```

```
gcgagagcca gtgcagccgc agtcctggca ggttacagga atttggtcag tttagaggat    780
ttaataagtc cgtggaaaat ttgtttctgt ctcttgctac ccacgtgaaa aagctctcca    840
aatcccagaa tgatatgact tctgagaagc atcttctcgc cacgggcccc aggcagtgtg    900
tgggacagac agagagacgg agccagtctg acactgcggt caacgtcacc accaggaagg    960
tcagtgcacc agatattctg aaacctctca atcaagagga tcccaaatgc tctactaacc   1020
ctattttgaa gcaacagaat ctcccatcca gtccggcacc cagtaccata ttctctggag   1080
gttttagaca cggaagttta attagcattg acagcacctg tacagagatg gcaattttg    1140 acaatgctaa tgtcactgga gaaatagaat ttgccattca ttattgcttc aaaacccatt   1200
ctttagaaat atgcatcaag gcctgtaaga accttgccta tggagaagaa agaagaaaa    1260 agtgcaatcc gtatgtgaag acctacctgt tgcccgacag atcctcccag ggaaagcgca   1320
agactggagt ccaaaggaac accgtggacc cgacctttca ggagaccttg aagtatcagg   1380
tggcccctgc ccagctggtg acccggcagc tgcaggtctc ggtgtggcat ctgggcacgc   1440
tggcccggag agtgtttctt ggagaagtga tcattcctct ggccacgtgg gactttgaag   1500
acagcacaac acagtccttc cgctggcatc cgctccgggc caaggcggag aaatacgaag   1560
acagcgttcc tcagagtaat ggagagctca cagtccgggc taagctggtt ctcccttcac   1620
ggcccagaaa actccaagag gctcaagaag gacagatca gccatcactt catggtcaac    1680
tttgtttggt agtgctagga gccaagaatt tacctgtgcg gccagatggc accttgaact   1740
catttgttaa gggctgtctc actctgccag accaacaaaa actgagactg aagtcgccag   1800
tcctgaggaa gcaggcttgc ccccagtgga acactcatt tgtcttcagt ggcgtaaccc    1860
cagctcagct gaggcagtcg agcttggagt taactgtctg ggatcaggcc tcttggaa     1920 tgaacgaccg cttgcttgga ggaaccagac ttggttcaaa gggagacaca gctgttggcg   1980
gggatgcatg ctcacaatcg aagctccagt ggcagaaagt ccttccagc cccaatctat     2040 ggacagacat gactcttgtc ctgcactgac atgaaggcct caaggttcca ggttgcagca   2100
ggcgtgaggc actgtgcgtc tgcagagggg ctacgaacca ggtgcagggt cccagctgga   2160 gaccccttg accttgagca gtctccatct gcggccctgt cccatggctt aaccgcctat    2220
tggtatctgt gtatatttac gttaaacaca attatgttac ctaagcctct ggtgggttat   2280
ctcctctttg agatgtagaa aatggccaga ttttaataaa cgttgttacc catgaaaaaa   2340
aaaaaaa                                                             2347
```

<210> SEQ ID NO 43
<211> LENGTH: 610
<212> TYPE: PRT
<213> ORGANISM: Homo sapiens
<220> FEATURE:
<223> OTHER INFORMATION: Delete:  this sequence is a duplicate of
      Sequence 13

<400> SEQUENCE: 43

```
Met Ala Gln Glu Ile Asp Leu Ser Ala Leu Lys Glu Leu Glu Arg Glu
 1               5                  10                  15

Ala Ile Leu Gln Val Leu Tyr Arg Asp Gln Ala Val Gln Asn Thr Glu
            20                  25                  30

Glu Glu Arg Thr Arg Lys Leu Lys Thr His Leu Gln His Leu Arg Trp
        35                  40                  45

Lys Gly Ala Lys Asn Thr Asp Trp Glu His Lys Glu Lys Cys Cys Ala
    50                  55                  60

Arg Cys Gln Gln Val Leu Gly Phe Leu Leu His Arg Gly Ala Val Cys
```

```
               65                  70                  75                  80
Arg Gly Cys Ser His Arg Val Cys Ala Gln Cys Arg Val Phe Leu Arg
                    85                  90                  95

Gly Thr His Ala Trp Lys Cys Thr Val Cys Phe Glu Asp Arg Asn Val
                100                 105                 110

Lys Ile Lys Thr Gly Glu Trp Phe Tyr Glu Arg Ala Lys Lys Phe
                115                 120                 125

Pro Thr Gly Gly Lys His Glu Thr Val Gly Gly Gln Leu Leu Gln Ser
                130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Leu Gln Glu Phe
                165                 170                 175

Gly Gln Phe Arg Gly Phe Asn Lys Ser Val Glu Asn Leu Phe Leu Ser
                180                 185                 190

Leu Ala Thr His Val Lys Lys Leu Ser Lys Ser Gln Asn Asp Met Thr
                195                 200                 205

Ser Glu Lys His Leu Leu Ala Thr Gly Pro Arg Gln Cys Val Gly Gln
210                 215                 220

Thr Glu Arg Arg Ser Gln Ser Asp Thr Ala Val Asn Val Thr Thr Arg
225                 230                 235                 240

Lys Val Ser Ala Pro Asp Ile Leu Lys Pro Leu Asn Gln Glu Asp Pro
                245                 250                 255

Lys Cys Ser Thr Asn Pro Ile Leu Lys Gln Gln Asn Leu Pro Ser Ser
                260                 265                 270

Pro Ala Pro Ser Thr Ile Phe Ser Gly Gly Phe Arg His Gly Ser Leu
                275                 280                 285

Ile Ser Ile Asp Ser Thr Cys Thr Glu Met Gly Asn Phe Asp Asn Ala
290                 295                 300

Asn Val Thr Gly Glu Ile Glu Phe Ala Ile His Tyr Cys Phe Lys Thr
305                 310                 315                 320

His Ser Leu Glu Ile Cys Ile Lys Ala Cys Lys Asn Leu Ala Tyr Gly
                325                 330                 335

Glu Glu Lys Lys Lys Lys Cys Asn Pro Tyr Val Lys Thr Tyr Leu Leu
                340                 345                 350

Pro Asp Arg Ser Ser Gln Gly Lys Arg Lys Thr Gly Val Gln Arg Asn
                355                 360                 365

Thr Val Asp Pro Thr Phe Gln Glu Thr Leu Lys Tyr Gln Val Ala Pro
370                 375                 380

Ala Gln Leu Val Thr Arg Gln Leu Gln Val Ser Val Trp His Leu Gly
385                 390                 395                 400

Thr Leu Ala Arg Arg Val Phe Leu Gly Glu Val Ile Ile Pro Leu Ala
                405                 410                 415

Thr Trp Asp Phe Glu Asp Ser Thr Gln Ser Phe Arg Trp His Pro
                420                 425                 430

Leu Arg Ala Lys Ala Glu Lys Tyr Glu Asp Ser Val Pro Gln Ser Asn
                435                 440                 445

Gly Glu Leu Thr Val Arg Ala Lys Leu Val Leu Pro Ser Arg Pro Arg
                450                 455                 460

Lys Leu Gln Glu Ala Gln Glu Gly Thr Asp Gln Pro Ser Leu His Gly
465                 470                 475                 480

Gln Leu Cys Leu Val Val Leu Gly Ala Lys Asn Leu Pro Val Arg Pro
                485                 490                 495
```

```
Asp Gly Thr Leu Asn Ser Phe Val Lys Gly Cys Leu Thr Leu Pro Asp
            500                 505                 510

Gln Gln Lys Leu Arg Leu Lys Ser Pro Val Leu Arg Lys Gln Ala Cys
        515                 520                 525

Pro Gln Trp Lys His Ser Phe Val Phe Ser Gly Val Thr Pro Ala Gln
        530                 535                 540

Leu Arg Gln Ser Ser Leu Glu Leu Thr Val Trp Asp Gln Ala Leu Phe
545                 550                 555                 560

Gly Met Asn Asp Arg Leu Leu Gly Gly Thr Arg Leu Gly Ser Lys Gly
                565                 570                 575

Asp Thr Ala Val Gly Gly Asp Ala Cys Ser Gln Ser Lys Ser Leu Gln Trp
        580                 585                 590

Gln Lys Val Leu Ser Ser Pro Asn Leu Trp Thr Asp Met Thr Leu Val
        595                 600                 605

Leu His
    610

<210> SEQ ID NO 44
<211> LENGTH: 1648
<212> TYPE: DNA
<213> ORGANISM: Homo sapiens
<220> FEATURE:
<223> OTHER INFORMATION: Delete: this sequence is a duplicate of
      Sequence 14

<400> SEQUENCE: 44
gaaatcatgc ccctcgtaga gcagcaggtc aagcagggc tgctggctat ttttccaaaa      60
agtgaggcag tttaaaaaaa aggcggagaa ctagaattat agaataatgg cacattttgt     120
gtatttgtaa aactaacggc ttgcatggtt cacaacccat ttcttatgcc tgtgttttcc     180
ttggcagcaa aatttctgtg gttcctccta ctccacctcc tgtcagcgag agccagtgca     240
gccgcagtcc tggcaggaag gtcagtgcac cagatattct gaaacctctc aatcaagagg     300
atcccaaatg ctctactaac cctatttga agcaacagaa tctcccatcc agtccggcac      360
ccagtaccat attctctgga ggttttagac acggaagttt aattagcatt gacagcacct     420
gtacagagat gggcaatttt gacaatgcta atgtcactgg agaaatagaa tttgccattc     480
attattgctt caaaacccat tctttagaaa tatgcatcaa ggcctgtaag aaccttgcct     540
atggagaaga aagaagaaa aagtgcaatc cgtatgtgaa gacctacctg ttgcccgaca     600
gatcctccca gggaaagcgc aagactggag tccaaaggaa caccgtggac ccgacctttc     660
aggagaccct tgaagtatcag gtggccctg cccagctggt gacccggcag ctgcaggtct     720
cggtgtggca tctgggcacg ctggcccgga gagtgtttct tggagaagtg atcattcctc     780
tggccacgtg ggactttgaa gacagcacaa cacagtcctt ccgctggcat ccgctccggg     840
ccaaggcgga gaaatacgaa gacagcgttc ctcagagtaa tggagagctc acagtccggg     900
ctaagctggt tctcccttca cggcccagaa aactccaaga ggctcaagaa gggacagatc     960
agccatcact tcatggtcaa ctttgtttgg tagtgctagg agccaagaat ttacctgtgc    1020
ggccagatgg cacccttgaac tcatttgtta agggctgtct cactctgcca gaccaacaaa    1080
aactgagact gaagtcgcca gtcctgagga gcaggcttg ccccagtgg aaacactcat     1140 ttgtcttcag tggcgtaacc ccagctcagc tgaggcagtc gagcttggag ttaactgtct    1200
gggatcaggc cctctttgga atgaacgacc gcttgcttgg aggaaccaga cttggttcaa    1260
agggagacac agctgttggc ggggatgcat gctcacaatc gaagctccag tggcagaaag    1320 tccttttccag ccccaatcta tggacagaca tgactcttgt cctgcactga catgaaggcc    1380
```

| | | |
|---|---|---|
| tcaaggttcc aggttgcagc aggcgtgagg cactgtgcgt ctgcagaggg gctacgaacc | 1440 |
| aggtgcaggg tcccagctgg agacccettt gaccttgagc agtctccatc tgcggccctg | 1500 |
| tcccatggct taaccgccta ttggtatctg tgtatattta cgttaaacac aattatgtta | 1560 |
| cctaagcctc tggtgggtta tctcctcttt gagatgtaga aaatggccag attttaataa | 1620 |
| acgttgttac ccatgaaaaa aaaaaaaa | 1648 |

<210> SEQ ID NO 45
<211> LENGTH: 313
<212> TYPE: PRT
<213> ORGANISM: Homo sapiens
<220> FEATURE:
<223> OTHER INFORMATION: Delete: this sequence is a duplicate of
      Sequence 15

<400> SEQUENCE: 45

Met Gly Asn Phe Asp Asn Ala Asn Val Thr Gly Glu Ile Glu Phe Ala
1               5                   10                  15

Ile His Tyr Cys Phe Lys Thr His Ser Leu Glu Ile Cys Ile Lys Ala
            20                  25                  30

Cys Lys Asn Leu Ala Tyr Gly Glu Lys Lys Lys Cys Asn Pro
        35                  40                  45

Tyr Val Lys Thr Tyr Leu Leu Pro Asp Arg Ser Gln Gly Lys Arg
    50                  55                  60

Lys Thr Gly Val Gln Arg Asn Thr Val Asp Pro Thr Phe Gln Glu Thr
65                  70                  75                  80

Leu Lys Tyr Gln Val Ala Pro Ala Gln Leu Val Thr Arg Gln Leu Gln
                85                  90                  95

Val Ser Val Trp His Leu Gly Thr Leu Ala Arg Arg Val Phe Leu Gly
            100                 105                 110

Glu Val Ile Ile Pro Leu Ala Thr Trp Asp Phe Glu Asp Ser Thr Thr
        115                 120                 125

Gln Ser Phe Arg Trp His Pro Leu Arg Ala Lys Ala Glu Lys Tyr Glu
    130                 135                 140

Asp Ser Val Pro Gln Ser Asn Gly Glu Leu Thr Val Arg Ala Lys Leu
145                 150                 155                 160

Val Leu Pro Ser Arg Pro Arg Lys Leu Gln Glu Ala Gln Glu Gly Thr
                165                 170                 175

Asp Gln Pro Ser Leu His Gly Gln Leu Cys Leu Val Val Leu Gly Ala
            180                 185                 190

Lys Asn Leu Pro Val Arg Pro Asp Gly Thr Leu Asn Ser Phe Val Lys
        195                 200                 205

Gly Cys Leu Thr Leu Pro Asp Gln Gln Lys Leu Arg Leu Lys Ser Pro
    210                 215                 220

Val Leu Arg Lys Gln Ala Cys Pro Gln Trp Lys His Ser Phe Val Phe
225                 230                 235                 240

Ser Gly Val Thr Pro Ala Gln Leu Arg Gln Ser Ser Leu Glu Leu Thr
                245                 250                 255

Val Trp Asp Gln Ala Leu Phe Gly Met Asn Asp Arg Leu Leu Gly Gly
            260                 265                 270

Thr Arg Leu Gly Ser Lys Gly Asp Thr Ala Val Gly Gly Asp Ala Cys
        275                 280                 285

Ser Gln Ser Lys Leu Gln Trp Gln Lys Val Leu Ser Ser Pro Asn Leu
    290                 295                 300

Trp Thr Asp Met Thr Leu Val Leu His

<210> SEQ ID NO 46
<211> LENGTH: 21
<212> TYPE: DNA
<213> ORGANISM: Artificial Sequence
<220> FEATURE:
<223> OTHER INFORMATION: Description of the artificial sequence: oligonucleotide

<400> SEQUENCE: 46
tcgtagagca gcaggtccaa g                                          21

<210> SEQ ID NO 47
<211> LENGTH: 1945
<212> TYPE: DNA
<213> ORGANISM: Homo sapiens

<400> SEQUENCE: 47
aatggaaggg cgtgagcgct tggtccatgc agtgaagctc ttccaacctg ggtcaacgaa      60
aacggagaag aaatggccca agaaatagat ctgagtgctc tcaaggagtt agaacgcgag     120
gccattctcc aggtcctgta ccgagaccag gcggttcaaa acacagagga ggagaggaca     180
cggaaactga aaacacacct gcagcatctc cggtggaaag gagcgaagaa cacggactgg     240
gagcacaaag agaagtgctg tgcgcgctgc cagcaggtgc tggggttcct gctgcaccgg     300
ggcgccgtgt gccggggctg cagccaccgc gtgtgtgccc agtgccgagt gttcctgagg     360
gggacccatg cctggaagtg cacggtgtgc ttcgaggaca ggaatgtcaa aataaaaact     420
ggagaatggt tctatgagga acgagccaag aaatttccaa ctggaggcaa acatgagaca     480
gttggagggc agctcttgca atcttatcag aagctgagca aaatttctgt ggttcctcct     540
actccacctc ctgtcagcga gagccagtgc agccgcagtc ctggcaggtt acaggaattt     600
ggtcagttta gaggatttaa taagtccgtg gaaaatttgt ttctgtctct tgctacccac     660
gtgaaaaagc tctccaaatc ccagaatgat atgacttctg agaagcatct tctcgccacg     720
ggccccaggc agtgtgtggg acagacgag agacggagcc agtctgacac tgcggtcaac     780
gtcaccacca ggaaggtcag tgcaccagat attctgaaac ctctcaatca agaggatccc     840
aaaatgctcta ctaaccctat tttgaagcaa cagaatctcc catccagtcc ggcacccagt     900
accatattct ctggaggttt tagacacgga agtttaatta gcattgacag cacctgtaca     960
gagatgggca atttttgacaa tgctaatgtc actggagaaa tagaatttgc cattcattat    1020
tgcttcaaaa cccattcttt agaaatatgc atcaaggcct gtaagaacct tgcctatgga    1080
gaagaaaaga gaaaaagtg caatccgtat gtgaagacct acctgttgcc cgacagatcc    1140
tcccagggaa agcgcaagac tggagtccaa aggaacaccg tggacccgac ctttcaggag    1200
accttgaagt atcaggtggc ccctgcccag ctggtgaccc ggcagctgca ggtctcggtg    1260
tggcatctgg gcacgctggc ccggagagtg tttcttggag aagtgatcat tcctctggcc    1320
acgtgggact ttgaagacag cacaacacag tccttccgct ggcatccgct ccgggccaag    1380
gcggagaaat acgaagacag cgttcctcag agtaatggag agctcacagt ccgggctaag    1440
ctggttctcc cttcacggcc cagaaaactc aagaggctc aagaagggac agatcagcca    1500
tcacttcatg gtcaactttg tttggtagtg ctaggagcca agaatttacc tgtgcggcca    1560
gatggcacct tgaactcatt tgttaagggc tgtctcactc tgccagacca acaaaaactg    1620
agactgaagt cgccagtcct gaggaagcag gcttgccccc agtggaaaca ctcatttgtc    1680
ttcagtggcg taaccccagc tcagctgagg cagtcgagct tggagttaac tgtctgggat    1740

```
caggccctct tggaatgaa cgaccgcttg cttggaggaa ccagacttgg ttcaaaggga   1800
gacacagctg ttggcgggga tgcatgctca caatcgaagc tccagtggca gaaagtcctt   1860
tccagcccca atctatggac agacatgact cttgtcctgc actgacatga aggcctcaag   1920
gttccaggtt gcagcaggcg tgagg                                          1945
```

```
<210> SEQ ID NO 48
<211> LENGTH: 610
<212> TYPE: PRT
<213> ORGANISM: Homo sapiens

<400> SEQUENCE: 48

Met Ala Gln Glu Ile Asp Leu Ser Ala Leu Lys Glu Leu Arg Glu
  1               5                  10                  15

Ala Ile Leu Gln Val Leu Tyr Arg Asp Gln Ala Val Gln Asn Thr Glu
                 20                  25                  30

Glu Glu Arg Thr Arg Lys Leu Lys Thr His Leu Gln His Leu Arg Trp
             35                  40                  45

Lys Gly Ala Lys Asn Thr Asp Trp Glu His Lys Glu Lys Cys Cys Ala
         50                  55                  60

Arg Cys Gln Gln Val Leu Gly Phe Leu Leu His Arg Gly Ala Val Cys
     65                  70                  75                  80

Arg Gly Cys Ser His Arg Val Cys Ala Gln Cys Arg Val Phe Leu Arg
                 85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
        115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160

Val Ser Glu Ser Gln Cys Ser Arg Ser Pro Gly Arg Leu Gln Glu Phe
                165                 170                 175

Gly Gln Phe Arg Gly Phe Asn Lys Ser Val Glu Asn Leu Phe Leu Ser
            180                 185                 190

Leu Ala Thr His Val Lys Lys Leu Ser Lys Ser Gln Asn Asp Met Thr
        195                 200                 205

Ser Glu Lys His Leu Leu Ala Thr Gly Pro Arg Gln Cys Val Gly Gln
    210                 215                 220

Thr Glu Arg Arg Ser Gln Ser Asp Thr Ala Val Asn Val Thr Thr Arg
225                 230                 235                 240

Lys Val Ser Ala Pro Asp Ile Leu Lys Pro Leu Asn Gln Glu Asp Pro
                245                 250                 255

Lys Cys Ser Thr Asn Pro Ile Leu Lys Gln Asn Leu Pro Ser Ser
            260                 265                 270

Pro Ala Pro Ser Thr Ile Phe Ser Gly Gly Phe Arg His Gly Ser Leu
        275                 280                 285

Ile Ser Ile Asp Ser Thr Cys Thr Glu Met Gly Asn Phe Asp Asn Ala
    290                 295                 300

Asn Val Thr Gly Glu Ile Glu Phe Ala Ile His Tyr Cys Phe Lys Thr
305                 310                 315                 320

His Ser Leu Glu Ile Cys Ile Lys Ala Cys Lys Asn Leu Ala Tyr Gly
                325                 330                 335
```

```
Glu Lys Lys Lys Lys Cys Asn Pro Tyr Val Lys Thr Tyr Leu Leu
            340                 345                 350
Pro Asp Arg Ser Ser Gln Gly Lys Arg Lys Thr Gly Val Gln Arg Asn
        355                 360                 365
Thr Val Asp Pro Thr Phe Gln Glu Thr Leu Lys Tyr Gln Val Ala Pro
    370                 375                 380
Ala Gln Leu Val Thr Arg Gln Leu Gln Val Ser Val Trp His Leu Gly
385                 390                 395                 400
Thr Leu Ala Arg Arg Val Phe Leu Gly Glu Val Ile Ile Pro Leu Ala
                405                 410                 415
Thr Trp Asp Phe Glu Asp Ser Thr Gln Ser Phe Arg Trp His Pro
            420                 425                 430
Leu Arg Ala Lys Ala Glu Lys Tyr Glu Asp Ser Val Pro Gln Ser Asn
        435                 440                 445
Gly Glu Leu Thr Val Arg Ala Lys Leu Val Leu Pro Ser Arg Pro Arg
    450                 455                 460
Lys Leu Gln Glu Ala Gln Glu Gly Thr Asp Gln Pro Ser Leu His Gly
465                 470                 475                 480
Gln Leu Cys Leu Val Leu Gly Ala Lys Asn Leu Pro Val Arg Pro
                485                 490                 495
Asp Gly Thr Leu Asn Ser Phe Val Lys Gly Cys Leu Thr Leu Pro Asp
            500                 505                 510
Gln Gln Lys Leu Arg Leu Lys Ser Pro Val Leu Arg Lys Gln Ala Cys
        515                 520                 525
Pro Gln Trp Lys His Ser Phe Val Phe Ser Gly Val Thr Pro Ala Gln
    530                 535                 540
Leu Arg Gln Ser Ser Leu Glu Leu Thr Val Trp Asp Gln Ala Leu Phe
545                 550                 555                 560
Gly Met Asn Asp Arg Leu Leu Gly Gly Thr Arg Leu Gly Ser Lys Gly
                565                 570                 575
Asp Thr Ala Val Gly Gly Asp Ala Cys Ser Gln Ser Lys Leu Gln Trp
            580                 585                 590
Gln Lys Val Leu Ser Ser Pro Asn Leu Trp Asp Met Thr Leu Val
        595                 600                 605
Leu His
    610

<210> SEQ ID NO 49
<211> LENGTH: 1741
<212> TYPE: DNA
<213> ORGANISM: Homo sapiens

<400> SEQUENCE: 49
aatggaaggg cgtgagcgct tggtccatgc agtgaagctc ttccaacctg ggtcaacgaa      60
aacggagaag aaatggccca agaaatagat ctgagtgctc tcaaggagtt agaacgcgag     120
gccattctcc aggtcctgta ccgagaccag gcggttcaaa cacagagga ggagaggaca     180 cggaaactga aaacacacct gcagcatctc cggtggaaag gagcgaagaa cacggactgg     240
gagcacaaag agaagtgctg tgcgcgctgc cagcaggtgc tggggttcct gctgcaccgg     300
ggcgccgtgt gccggggctg cagccaccgc gtgtgtgccc agtgccgagt gttcctgagg     360
gggacccatg cctggaagtg cacggtgtgc ttcgaggaca ggaatgtcaa aataaaaact     420
ggagaatggt tctatgagga acgagccaag aaatttccaa ctggaggcaa acatgagaca     480
gttggagggc agctcttgca atcttatcag aagctgagca aaatttctgt ggttcctcct     540
```

-continued

```
actccacctc ctgtcagcga gagccagtgc agccgcagtc ctggcaggaa ggtcagtgca    600
ccagatattc tgaaacctct caatcaagag gatcccaaat gctctactaa ccctatttg    660
aagcaacaga atctcccatc cagtccggca cccagtacca tattctctgg aggttttaga    720
cacgaaagtt taattagcat tgacagcacc tgtacagaga tgggcaattt tgacaatgct    780
aatgtcactg gagaaataga atttgccatt cattattgct tcaaaaccca ttctttagaa    840
atatgcatca aggcctgtaa gaaccttgcc tatggagaag aaaagaagaa aaagtgcaat    900
ccgtatgtga agacctacct gttgcccgac agatcctccc agggaaagcg caagactgga    960
gtccaaagga acaccgtgga cccgaccttt caggagacct tgaagtatca ggtggcccct   1020
gcccagctgg tgacccggca gctgcaggtc tcggtgtggc atctgggcac gctggcccgg   1080
agagtgtttc ttggagaagt gatcattcct ctggccacgt gggactttga agacagcaca   1140
acacagtcct tccgctggca tccgctccgg gccaaggcgg agaaatacga agacagcgtt   1200
cctcagagta atggagagct cacagtccgg gctaagctgg ttctcccttc acggcccaga   1260
aaactccaag aggctcaaga agggacagat cagccatcac ttcatggtca actttgtttg   1320
gtagtgctag gagccaagaa tttacctgtg cggccagatg gcaccttgaa ctcatttgtt   1380
aagggctgtc tcactctgcc agaccaacaa aaactgagac tgaagtcgcc agtcctgagg   1440
aagcaggctt gccccagtg gaaacactca tttgtcttca gtggcgtaac cccagctcag   1500
ctgaggcagt cgagcttgga gttaactgtc tgggatcagg ccctctttgg aatgaacgac   1560
cgcttgcttg gaggaaccag acttggttca aagggagaca cagctgttgg cggggatgca   1620
tgctcacaat cgaagctcca gtggcagaaa gtcctttcca gccccaatct atggacagac   1680
atgactcttg tcctgcactg acatgaaggc ctcaaggttc caggttgcag caggcgtgag   1740
g                                                                  1741
```

<210> SEQ ID NO 50
<211> LENGTH: 542
<212> TYPE: PRT
<213> ORGANISM: Homo sapiens

<400> SEQUENCE: 50

```
Met Ala Gln Glu Ile Asp Leu Ser Ala Leu Lys Glu Leu Glu Arg Glu
  1               5                  10                  15

Ala Ile Leu Gln Val Leu Tyr Arg Asp Gln Ala Val Gln Asn Thr Glu
             20                  25                  30

Glu Glu Arg Thr Arg Lys Leu Lys Thr His Leu Gln His Leu Arg Trp
         35                  40                  45

Lys Gly Ala Lys Asn Thr Asp Trp Glu His Lys Glu Lys Cys Cys Ala
     50                  55                  60

Arg Cys Gln Gln Val Leu Gly Phe Leu Leu His Arg Gly Ala Val Cys
 65                  70                  75                  80

Arg Gly Cys Ser His Arg Val Cys Ala Gln Cys Arg Val Phe Leu Arg
                 85                  90                  95

Gly Thr His Ala Trp Lys Cys Thr Val Cys Phe Glu Asp Arg Asn Val
            100                 105                 110

Lys Ile Lys Thr Gly Glu Trp Phe Tyr Glu Glu Arg Ala Lys Lys Phe
        115                 120                 125

Pro Thr Gly Gly Lys His Glu Thr Val Gly Gly Gln Leu Leu Gln Ser
    130                 135                 140

Tyr Gln Lys Leu Ser Lys Ile Ser Val Val Pro Pro Thr Pro Pro Pro
145                 150                 155                 160
```

```
Val Ser Glu Ser Gln Cys Ser Arg Ser Pro Gly Arg Lys Val Ser Ala
            165                 170                 175

Pro Asp Ile Leu Lys Pro Leu Asn Gln Glu Asp Pro Lys Cys Ser Thr
            180                 185                 190

Asn Pro Ile Leu Lys Gln Gln Asn Leu Pro Ser Ser Pro Ala Pro Ser
            195                 200                 205

Thr Ile Phe Ser Gly Gly Phe Arg His Gly Ser Leu Ile Ser Ile Asp
            210                 215                 220

Ser Thr Cys Thr Glu Met Gly Asn Phe Asp Asn Ala Asn Val Thr Gly
225                 230                 235                 240

Glu Ile Glu Phe Ala Ile His Tyr Cys Phe Lys Thr His Ser Leu Glu
            245                 250                 255

Ile Cys Ile Lys Ala Cys Lys Asn Leu Ala Tyr Gly Glu Glu Lys Lys
            260                 265                 270

Lys Lys Cys Asn Pro Tyr Val Lys Thr Tyr Leu Leu Pro Asp Arg Ser
            275                 280                 285

Ser Gln Gly Lys Arg Lys Thr Gly Val Gln Arg Asn Thr Val Asp Pro
            290                 295                 300

Thr Phe Gln Glu Thr Leu Lys Tyr Gln Val Ala Pro Ala Gln Leu Val
305                 310                 315                 320

Thr Arg Gln Leu Gln Val Ser Val Trp His Leu Gly Thr Leu Ala Arg
            325                 330                 335

Arg Val Phe Leu Gly Glu Val Ile Ile Pro Leu Ala Thr Trp Asp Phe
            340                 345                 350

Glu Asp Ser Thr Thr Gln Ser Phe Arg Trp His Pro Leu Arg Ala Lys
            355                 360                 365

Ala Glu Lys Tyr Glu Asp Ser Val Pro Gln Ser Asn Gly Glu Leu Thr
            370                 375                 380

Val Arg Ala Lys Leu Val Leu Pro Ser Arg Pro Arg Lys Leu Gln Glu
385                 390                 395                 400

Ala Gln Glu Gly Thr Asp Gln Pro Ser Leu His Gly Gln Leu Cys Leu
            405                 410                 415

Val Val Leu Gly Ala Lys Asn Leu Pro Val Arg Pro Asp Gly Thr Leu
            420                 425                 430

Asn Ser Phe Val Lys Gly Cys Leu Thr Leu Pro Asp Gln Gln Lys Leu
            435                 440                 445

Arg Leu Lys Ser Pro Val Leu Arg Lys Gln Ala Cys Pro Gln Trp Lys
            450                 455                 460

His Ser Phe Val Phe Ser Gly Val Thr Pro Ala Gln Leu Arg Gln Ser
465                 470                 475                 480

Ser Leu Glu Leu Thr Val Trp Asp Gln Ala Leu Phe Gly Met Asn Asp
            485                 490                 495

Arg Leu Leu Gly Gly Thr Arg Leu Gly Ser Lys Gly Asp Thr Ala Val
            500                 505                 510

Gly Gly Asp Ala Cys Ser Gln Ser Lys Leu Gln Trp Gln Lys Val Leu
            515                 520                 525

Ser Ser Pro Asn Leu Trp Thr Asp Met Thr Leu Val Leu His
530                 535                 540
```